(12) United States Patent
Klar et al.

(10) Patent No.: US 8,987,239 B2
(45) Date of Patent: Mar. 24, 2015

(54) 19-NOR-STEROID DERIVATIVES WITH A 15α,16α-METHYLENE GROUP AND A SATURATED 17,17-SPIROLACTONE RING, USE THEREOF, AND MEDICAMENTS CONTAINING SAID DERIVATIVES

(71) Applicant: Bayer Intellectual Property GmbH, Monheim (DE)

(72) Inventors: Ulrich Klar, Berlin (DE); Joachim Kuhnke, Potsdam (DE); Rolf Bohlmann, Berlin (DE); Jan Hübner, Berlin (DE); Sven Ring, Jena (DE); Thomas Frenzel, Hofheim (DE); Frederik Menges, Schriesheim (DE); Steffen Borden, Berlin (DE); Hans-Peter Muhn, Berlin (DE); Katja Prelle, Berlin (DE)

(73) Assignee: Bayer Intellectual Property GbmH, Monheim (DE)

( * ) Notice: Subject to any disclaimer, the term of this patent is extended or adjusted under 35 U.S.C. 154(b) by 0 days.

(21) Appl. No.: 13/738,751

(22) Filed: Jan. 10, 2013

(65) Prior Publication Data

US 2013/0123219 A1    May 16, 2013

Related U.S. Application Data

(63) Continuation of application No. 12/810,860, filed as application No. PCT/EP2008/011165 on Dec. 23, 2008, now abandoned.

(30) Foreign Application Priority Data

Dec. 29, 2007    (DE) .................. 10 2007 063 495

(51) Int. Cl.
| | | |
|---|---|---|
| *A61K 31/58* | (2006.01) | |
| *C07J 21/00* | (2006.01) | |
| *C07J 53/00* | (2006.01) | |

(52) U.S. Cl.
CPC ............ *C07J 21/003* (2013.01); *C07J 53/008* (2013.01)
USPC ............................ 514/173; 540/41

(58) Field of Classification Search
USPC ............................ 540/41; 514/173
See application file for complete search history.

(56) References Cited

U.S. PATENT DOCUMENTS

| 4,584,288 A | 4/1986 | Nickish et al. |
| 2009/0029953 A1 | 1/2009 | Bohlmann et al. |

FOREIGN PATENT DOCUMENTS

| EP | 0 150 157 A2 | 7/1985 |
| WO | WO 2006/072467 A1 | 7/2006 |

OTHER PUBLICATIONS

International Search Report of PCT/EP2008/011165 (Jul. 2, 2009).
Fatma Kandemirli, Nesrin Tokay, Nataly M. Shvets, Anatoly S. Dimoglo, "Investigation of structure-activity relationship on 17-spirolactone derivatives: the electronic-topological approach," Il Farmaco, vol. 57, pp. 601-607 (2002).

*Primary Examiner* — Barbara P Badio
(74) *Attorney, Agent, or Firm* — Thomas C. Blankinship

(57) ABSTRACT

The 15α,16α-methylene-17-hydroxy-19-nor-17-pregna-4-en-3-one-21-carboxylic acid γ-lactone derivatives of the present invention possess progestational efficacy. They have the general chemical formula I, in which Z is selected from the group comprising an oxygen atom, two hydrogen atoms, NOR and NNHSO$_2$R, where R is hydrogen, $C_1$-$C_{10}$-alkyl, aryl or $C_7$-$C_{20}$-aralkyl, $R^4$ is hydrogen or halogen, and moreover either: $R^{6a}$, $R^{6b}$ together form methylene or 1,2-ethanediyl or $R^{6a}$ is hydrogen and $R^{6b}$ is selected from the group comprising hydrogen, $C_1$-$C_{10}$-alkyl, $C_2$-$C_{10}$-alkenyl or $C_2$-$C_{10}$-alkynyl, and $R^7$ is selected from the group comprising hydrogen, $C_1$-$C_{10}$-alkyl, $C_3$-$C_6$-cycloalkyl, $C_2$-$C_{10}$-alkenyl or $C_2$-$C_{10}$-alkynyl, or: $R^{6a}$ is hydrogen and $R^{6b}$ and $R^7$, together, denote a bond, an oxygen or form methylene, $R^{18}$ represents hydrogen or $C_1$-$C_3$-alkyl and in addition include their solvates, hydrates, stereoisomers and salts.

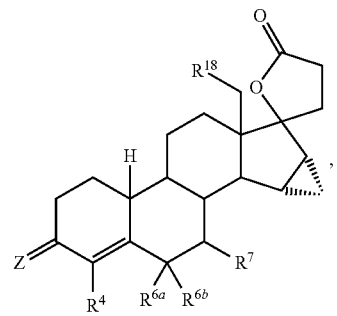

I

9 Claims, No Drawings

19-NOR-STEROID DERIVATIVES WITH A 15α,16α-METHYLENE GROUP AND A SATURATED 17,17-SPIROLACTONE RING, USE THEREOF, AND MEDICAMENTS CONTAINING SAID DERIVATIVES

The invention relates to 15α,16α-methylene-17-hydroxy-19-nor-17-pregna-4-en-3-one-21-carboxylic acid γ-lactone derivatives with progestational action, use thereof and medicinal products containing the derivatives, for example for the treatment of pre-, peri- and postmenopausal and of premenstrual complaints.

Compounds with progestational, antimineralocorticoid, antiandrogenic or antiestrogenic action based on a steroid structure are known from the literature, derived for example from 19-nor-androst-4-en-3-one or a derivative thereof (the numbering of the steroid structure is given for example in Fresenius/Görlitzer 3rd Ed. 1991 "Organic Chemical Nomenclature" p. 60 ff.).

Thus, WO 2006072467 A1 discloses the compound 6β,7β-15β,16β-dimethylene-3-oxo-17-pregn-4-ene-21,17β-carbolactone (drospirenone), which has progestational action and has been used for example in an oral contraceptive and in a preparation for the treatment of postmenopausal complaints. Owing to its comparatively low affinity for the progestogen receptor and its comparatively high ovulation-inhibiting dose, however, drospirenone is contained in the contraceptive at the relatively high daily dose of 3 mg. Drospirenone is, moreover, also characterized in that in addition to the progestational action it also has aldosterone-antagonistic (antimineralocorticoid) and antiandrogenic action. These two properties make drospirenone very similar in its pharmacological profile to the natural progestogen, progesterone, which however, unlike drospirenone, is not sufficiently bioavailable orally. In order to lower the dose to be administered, WO 2006072467 A1 further proposes an 18-methyl-19-nor-17-pregn-4-ene-21,17-carbolactone and pharmaceutical preparations containing this, which have a higher progestational potency than drospirenone.

In addition, U.S. Pat. No. 3,705,179, for example, discloses steroids that display antiandrogenic activity and are suitable for the treatment of diseases that are linked to androgens.

The aim of the present invention is to make compounds available that bind strongly, and preferably more strongly than drospirenone, to the progestogen receptor. Moreover, the compounds should preferably also have antimineralocorticoid action and, with respect to the androgen receptor, a neutral to slightly androgenic action. Another essential aim of the present invention consists of achieving a balanced action profile with respect to the progestational action to the antimineralocorticoid action, so that the ratio of the progestational action to the antimineralocorticoid action is less than with drospirenone.

This aim is achieved with the 15α,16α-methylene-17-hydroxy-19-nor-17-pregna-4-en-3-one-21-carboxylic acid γ-lactone derivatives according to the invention, the use of the derivatives according to the invention and a medicinal product containing at least one derivative according to the invention. Advantageous embodiments of the invention are presented in the subclaims.

The present invention describes the novel 15,16-methylene-17-hydroxy-19-nor-17-pregna-4,20(Z)-dien-3-one-21-carboxylic acid γ-lactone derivatives of general formula I,

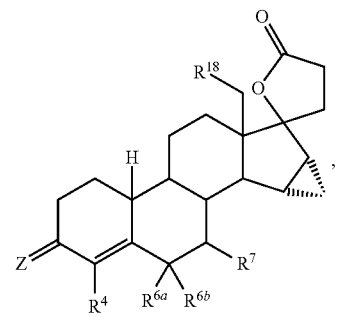

in which
Z denotes oxygen, two hydrogen atoms, a group =NOR$^1$ or =NNHSO$_2$R$^1$,
R$^1$ denotes hydrogen, C$_1$-C$_{10}$-alkyl, aryl, C$_7$-C$_{20}$-aralkyl,
R$^4$ denotes hydrogen or halogen,
R$^{6a}$, R$^{6b}$ which may be identical or different, denote hydrogen, C$_1$-C$_{10}$-alkyl, C$_2$-C$_{10}$-alkenyl, C$_2$-C$_{10}$-alkynyl or together denote methylene or 1,2-ethanediyl,
R$^7$ denotes hydrogen, C$_1$-C$_{10}$-alkyl, C$_3$-C$_6$-cycloalkyl, C$_2$-C$_{10}$-alkenyl, C$_2$-C$_{10}$-alkynyl,
R$^{6a}$, R$^7$ together, denote a bond, an oxygen or a methylene group,
R$^{18}$ denotes hydrogen, C$_1$-C$_3$-alkyl.
The residues R$^{6a}$, R$^{6b}$ and R$^7$ and the three-membered ring can each be in the α or β position.

Compounds of formula I are preferred in which
Z denotes oxygen, a group =NOR$^1$,
R$^1$ denotes hydrogen, C$_1$-C$_6$-alkyl, aryl, C$_7$-C$_{12}$-aralkyl,
R$^4$ denotes hydrogen or halogen,
R$^{6a}$, R$^{6b}$ which may be identical or different, denote hydrogen, C$_1$-C$_6$-alkyl, C$_2$-C$_6$-alkenyl, C$_2$-C$_6$-alkynyl or together denote methylene or 1,2-ethanediyl,
R$^7$ denotes hydrogen, C$_1$-C$_6$-alkyl, C$_3$-C$_6$-cycloalkyl, C$_2$-C$_6$-alkenyl, C$_2$-C$_6$-alkynyl,
R$^{6a}$, R$^7$ together, denote a bond, or a methylene group,
R$^{18}$ denotes hydrogen, C$_1$-C$_2$-alkyl.

Compounds of formula I are especially preferred in which
Z denotes oxygen, a group =NOR$^1$,
R$^1$ denotes hydrogen, C$_1$-C$_3$-alkyl,
R$^4$ denotes hydrogen, chlorine or bromine,
R$^{6a}$, R$^{6b}$ which may be identical or different, denote hydrogen, C$_1$-C$_3$-alkyl, C$_2$-C$_4$-alkenyl, or together denote methylene or together denote 1,2-ethanediyl,
R$^7$ denotes hydrogen, C$_1$-C$_4$-alkyl, C$_3$-C$_4$-cycloalkyl, C$_2$-C$_4$-alkenyl,
R$^{6a}$, R$^7$ together, denote a bond, or a methylene group,
R$^{18}$ denotes hydrogen, methyl.

The numbering of the carbon backbone of the derivatives according to the invention with the general chemical formula I follows the numbering of a steroid structure in the usual way, as described for example in Fresenius, loc. cit. The numbering of the residues stated in the claims corresponds in a similar manner to their bonding position on the carbon backbone of the derivative, as far as this relates to R$^4$, R$^6$, R$^7$ and R$^{18}$. For example, the residue R$^4$ binds to the C$^4$-position of the derivative according to the invention.

With respect to the groups defined for Z, the groups NOR' and NNHSO$_2$R' each bind with a double bond via N to the carbon backbone of the derivative according to =NOR' or =NNH—SO$_2$R'. OR' in NOR' and NHSO$_2$R' in NNHSO$_2$R' can be in syn- or anti-position.

Alkyl groups $R^1$, $R^{6a}$, $R^{6b}$, $R^7$, $R^{18}$, $R^{19}$, $R^{20}$, $R^{21a}$, $R^{21b}$ and $R^{22}$ are to be considered to be linear or branched alkyl groups with 1-10 carbon atoms, for example methyl, ethyl, propyl, isopropyl, butyl, isobutyl, tert.-butyl, pentyl, isopentyl, neopentyl, heptyl, hexyl, decyl.

The alkyl groups $R^1$, $R^{6a}$, $R^{6b}$, $R^7$, $R^{18}$, $R^{19}$, $R^{20}$, $R^{21a}$, $R^{21b}$ and $R^{22}$ can be perfluorinated or can be substituted with 1-5 halogen atoms, hydroxyl groups, $C_1$-$C_4$-alkoxy groups, $C_6$-$C_{12}$-aryl groups (which can be substituted with 1-3 halogen atoms).

Alkenyl groups $R^{6a}$ and $R^{6b}$ are to be considered to be linear or branched alkene groups with 2-10 carbon atoms, such as for example vinyl, propenyl, butenyl, pentenyl, isobutenyl, isopentenyl.

Alkynyl groups $R^{6a}$ and $R^{6b}$ are to be considered to be linear or branched alkyne groups with 2-10 carbon atoms, such as for example ethynyl, propynyl, butynyl, pentynyl, isobutynyl, isopentynyl.

The alkenyl and alkynyl groups $R^{6a}$ and $R^{6b}$ can be substituted with 1-5 halogen atoms, hydroxyl groups, $C_1$-$C_3$-alkoxy groups, $C_6$-$C_{12}$-aryl groups (which can be substituted with 1-3 halogen atoms).

As cycloalkyl groups $R^7$, consideration may be given to cyclopropyl, cyclobutyl, cyclopentyl, cyclohexyl.

The cycloalkyl groups $R^7$ can be substituted with halogen, OH, O-alkyl, $CO_2H$, $CO_2$-alkyl, —$NH_2$, —$NO_2$, —$N_3$, —CN, $C_1$-$C_{10}$-alkyl, $C_1$-$C_{10}$-acyl, $C_1$-$C_{10}$-acyloxy groups.

As aryl residue $R^1$, $R^{6a}$, $R^{6b}$ and $R^7$, consideration may be given to substituted and unsubstituted carbocyclic or heterocyclic residues with one or more heteroatoms, e.g. phenyl, naphthyl, furyl, thienyl, pyridyl, pyrazolyl, pyrimidinyl, oxazolyl, pyridazinyl, pyrazinyl, quinolyl, thiazolyl, which can be singly or multiply substituted with halogen, OH, O-alkyl, $CO_2H$, $CO_2$-alkyl, —$NH_2$, —$NO_2$, —$N_3$, —CN, $C_1$-$C_{10}$-alkyl, $C_1$-$C_{10}$-acyl, $C_1$-$C_{10}$-acyloxy groups.

The aralkyl groups in $R^1$ and $R^7$ can contain up to 14, preferably 6 to 10, carbon atoms in the ring and 1 to 8, preferably 1 to 4, atoms in the alkyl chain. As aralkyl residues, consideration may be given for example to benzyl, phenylethyl, naphthylmethyl, naphthylethyl, furylmethyl, thienylethyl, pyridylpropyl. The rings can be singly or multiply substituted with halogen, OH, O-alkyl, $CO_2H$, $CO_2$-alkyl, —$NO_2$, —$N_3$, —CN, $C_1$-$C_{20}$-alkyl, $C_1$-$C_{20}$-acyl, $C_1$-$C_{20}$-acyloxy groups.

Halogen means fluorine, chlorine or bromine.

The derivatives with the general chemical formula I include all stereoisomers and mixtures thereof.

The derivatives according to the invention can also be in the form of solvates, in particular of hydrates, and the compounds according to the invention accordingly contain polar solvents, in particular water, as structural element of the crystal lattice of the compounds according to the invention. The polar solvent, in particular water, can be present in stoichiometric proportions or even in nonstoichiometric proportions. Stoichiometric solvates and hydrates are also called hemi-, (semi-), mono-, sesqui-, di-, tri-, tetra-, penta-, etc. solvates or hydrates.

It was found that the compounds or derivatives according to the invention have good progestational action. Furthermore, some interesting compounds according to the invention interact with the mineralocorticoid receptor and are able to impart an antagonistic action. Moreover, the compounds according to the invention have a neutral to slightly androgenic action with respect to the androgen receptor. Another property of the compounds is that the bonds of these compounds to the progesterone receptor and to the mineralocorticoid receptor are balanced relative to one another, namely so that the ratio of their capacity for binding to the progesterone receptor to the capacity for binding to the mineralocorticoid receptor is less than in the case of drospirenone. Therefore the antimineralocorticoid action of these compounds at given progestational action is less than with drospirenone. If the dosage of a given compound according to the invention is based on its progestational action, the antimineralocorticoid action of this compound at this dosage is therefore less than with drospirenone.

The compounds listed below are preferred according to the invention:

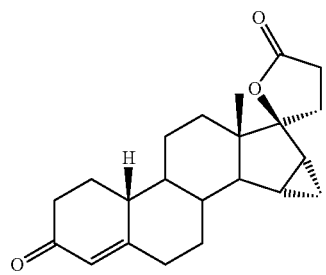

17β-Hydroxy-15α,16α-methylene-19-nor-17α-pregna-4-en-3-one-21-carboxylic acid γ-lactone

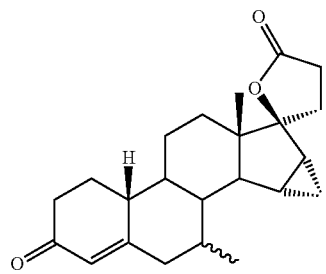

17β-Hydroxy-7α-methyl-15α,16α-methylene-19-nor-17α-pregna-4-en-3-one-21-carboxylic acid γ-lactone
17β-Hydroxy-7β-methyl-15α,16α-methylene-19-nor-17α-pregna-4-en-3-one-21-carboxylic acid γ-lactone

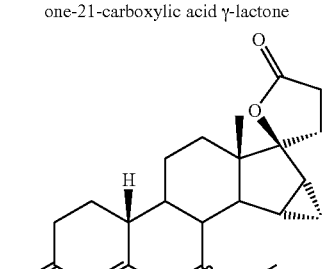

17β-Hydroxy-7α-ethyl-15α,16α-methylene-19-nor-17α-pregna-4-en-3-one-21-carboxylic acid γ-lactone
17β-Hydroxy-7β-ethyl-15α,16α-methylene-19-nor-17α-pregna-4-en-3-one-21-carboxylic acid γ-lactone

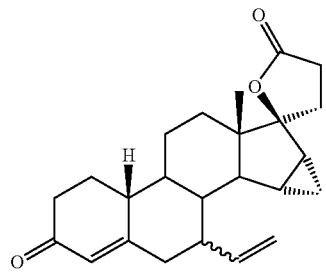

17β-Hydroxy-7α-vinyl-15α,16α-methylene-19-nor-17α-pregna-4-en-3-one-21-carboxylic acid γ-lactone
17β-Hydroxy-7β-vinyl-15α,16α-methylene-19-nor-17α-pregna-4-en-3-one-21-carboxylic acid γ-lactone

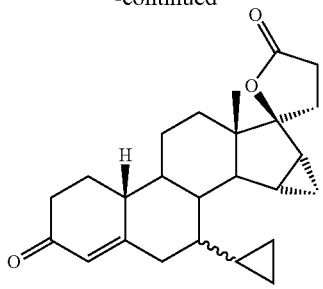

17β-Hydroxy-7α-cyclopropyl-15α,16α-methylene-19-nor-17α-pregna-4-en-3-one-21-carboxylic acid γ-lactone
17β-Hydroxy-7β-cyclopropyl-15α,16α-methylene-19-nor-17α-pregna-4-en-3-one-21-carboxylic acid γ-lactone

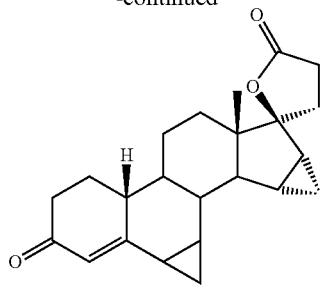

17β-Hydroxy-6α,7α,15α,16α-bismethylene-19-nor-17α-pregna-4-en-3-one-21-carboxylic acid γ-lactone
17β-Hydroxy-6β,7β,15α,16α-bismethylene-19-nor-17α-pregna-4-en-3-one-21-carboxylic acid γ-lactone

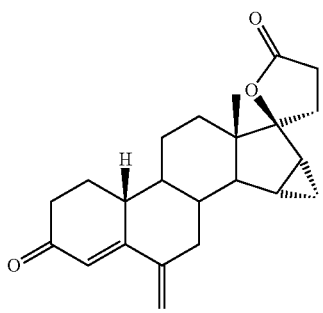

17β-Hydroxy-6-methylene-15α,16α-methylene-19-nor-17α-pregna-4-en-3-one-21-carboxylic acid γ-lactone

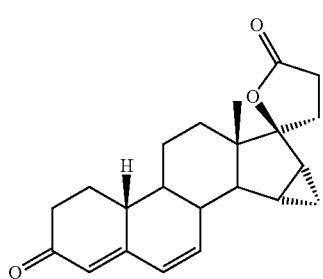

17β-Hydroxy-15α,16α-methylene-19-nor-17α-pregna-4,6-dien-3-one-21-carboxylic acid γ-lactone

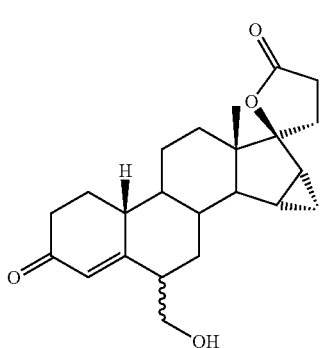

17β-Hydroxy-6α-hydroxymethyl-15α,16α-methylene-19-nor-17α-pregna-4-en-3-one-21-carboxylic acid γ-lactone
17β-Hydroxy-6β-hydroxymethyl-15α,16α-methylene-19-nor-17α-pregna-4-en-3-one-21-carboxylic acid γ-lactone

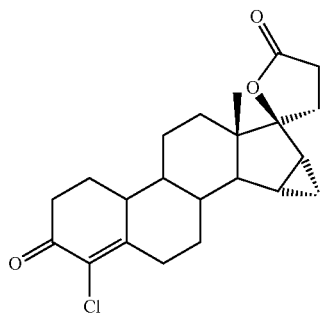

4-Chloro-17β-hydroxy-15α,16α-methylene-19-nor-17α-pregna-4-en-3-one-21-carboxylic acid γ-lactone

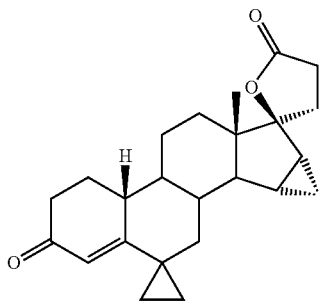

6,6-(1,2-Ethanediyl)-17β-hydroxy-15α,16α-methylene-19-nor-17α-pregna-4-en-3-one-21-carboxylic acid γ-lactone

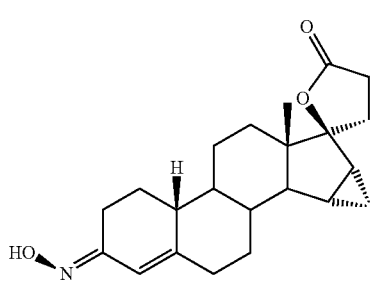

(E/Z)-3-(Hydroxyimino)-17β-hydroxy-15α,16α-methylene-19-nor-17α-pregna-4-ene-21-carboxylic acid γ-lactone -continued

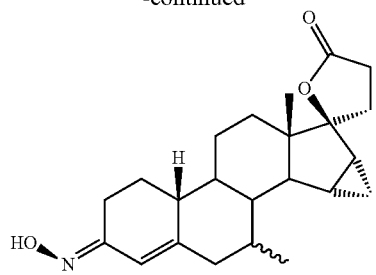

(E/Z)-3-(Hydroxyimino)-17β-hydroxy-7α-methyl-15α,16α-methylene-19-nor-17α-pregna-4-ene-21-carboxylic acid γ-lactone
(E/Z)-3-(Hydroxyimino)-17β-hydroxy-7β-methyl-15α,16α-methylene-19-nor-17α-pregna-4-ene-21-carboxylic acid γ-lactone

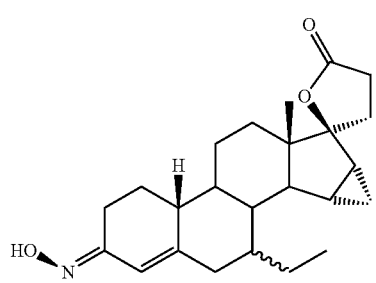

(E/Z)-3-(Hydroxyimino)-17β-hydroxy-7α-ethyl-15α,16α-methylene-19-nor-17α-pregna-4-ene-21-carboxylic acid γ-lactone
(E/Z)-3-(Hydroxyimino)-17β-hydroxy-7β-ethyl-15α,16α-methylene-19-nor-17α-pregna-4-ene-21-carboxylic acid γ-lactone

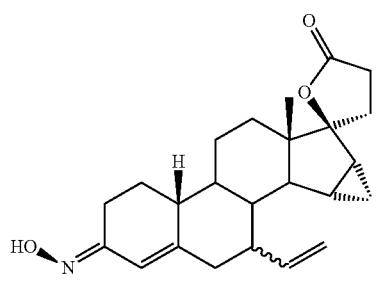

(E/Z)-3-(Hydroxyimino)-17β-hydroxy-7α-vinyl-15α,16α-methylene-19-nor-17α-pregna-4-ene-21-carboxylic acid γ-lactone
(E/Z)-3-(Hydroxyimino)-17β-hydroxy-7β-vinyl-15α,16α-methylene-19-nor-17α-pregna-4-any-21-carboxylic acid γ-lactone

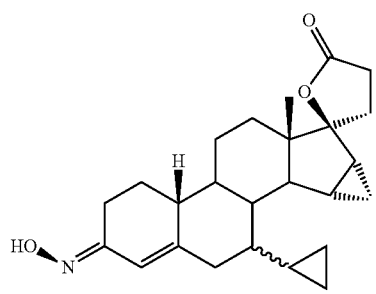

(E/Z)-3-(Hydroxyimino)-17β-hydroxy-7α-cyclopropyl-15α,16α-methylene-19-nor-17α-pregna-4-ene-21-carboxylic acid γ-lactone
(E/Z)-3-(Hydroxyimino)-17β-hydroxy-7β-cyclopropyl-15α,16α-methylene-19-nor-17α-pregna-4-ene-21-carboxylic acid γ-lactone -continued

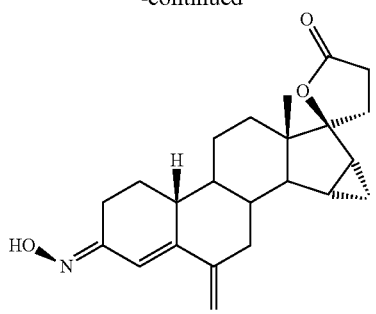

(E/Z)-3-(Hydroxyimino)-17β-hydroxy-6-methylene-15α,16α-methylene-19-nor-17α-pregna-4-ene-21-carboxylic acid γ-lactone

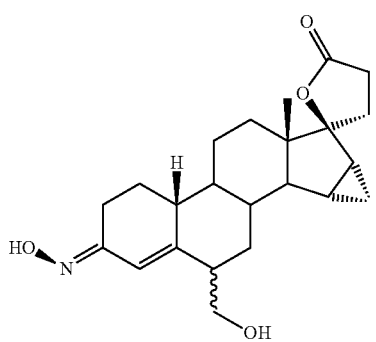

(E/Z)-3-(Hydroxyimino)-17β-hydroxy-6α-hydroxymethyl-15α,16α-methylene-19-nor-17α-pregna-4-ene-21-carboxylic acid γ-lactone
(E/Z)-3-(Hydroxyimino)-17β-hydroxy-6β-hydroxymethyl-15α,16α-methylene-19-nor-17α-pregna-4-ene-21-carboxylic acid γ-lactone

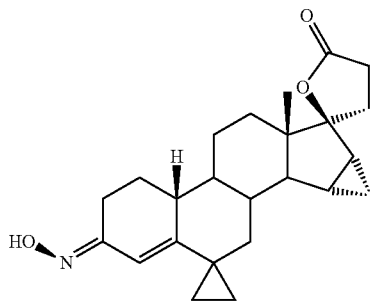

(E/Z)-3-(Hydroxyimino)-6,6-(1,2-ethanediyl)-17β-hydroxy-15α,16α-methylene-19-nor-17α-pregna-4-ene-21-carboxylic acid γ-lactone

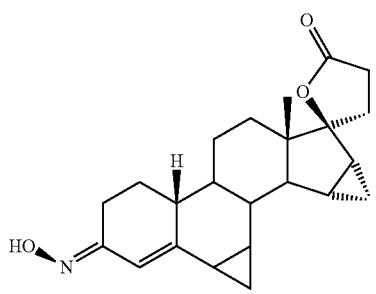

(E/Z)-3-(Hydroxyimino)-17β-hydroxy-6α,7α,15α,16α-bismethylene-19-nor-17α-pregna-4-ene-21-carboxylic acid γ-lactone
(E/Z)-3-(Hydroxyimino)-17β-hydroxy-6β,7β,15α,16α-bismethylene-19-nor-17α-pregna-4-ene-21-carboxylic acid γ-lactone -continued

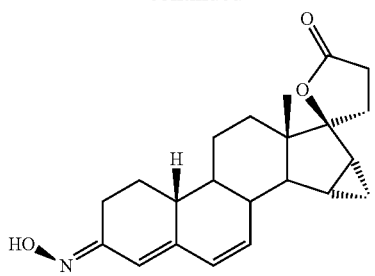

(E/Z)-3-(Hydroxyimino)-17β-hydroxy-15α,16α-
methylene-19-nor-17α-pregna-4,6-diene-21-carboxylic acid γ-lactone

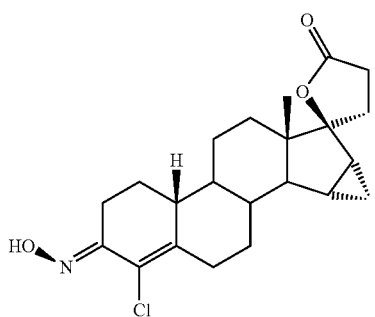

(E/Z)-3-(Hydroxyimino)-4-chloro-17β-Hydroxy-15α,16α-
methylene-19-nor-17α-pregna-4-ene-21-carboxylic acid γ-lactone

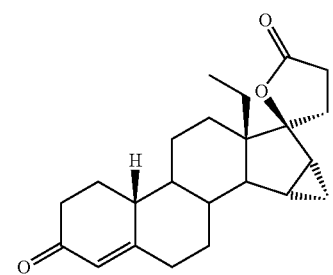

17β-Hydroxy-18-methyl-15α,16α-methylene-19-nor-17α-pregna-
4-en-3-one-21-carboxylic acid γ-lactone

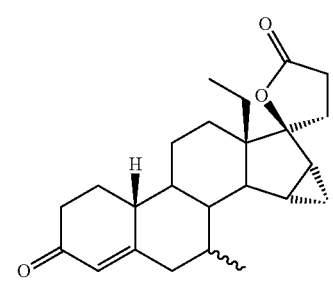

17β-Hydroxy-7α-methyl-18-methyl-15α,16α-methylene-19-nor-17α-
pregna-4-en-3-one-21-carboxylic acid γ-lactone
17β-Hydroxy-7β-methyl-18-methyl-15α,16α-methylene-19-nor-17α-
pregna-4-en-3-one-21-carboxylic acid γ-lactone -continued

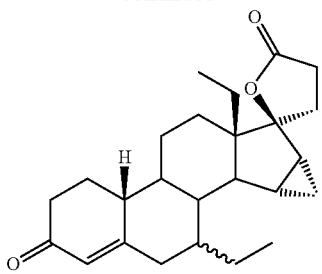

17β-Hydroxy-7α-ethyl-18-methyl-15α,16α-methylene-19-nor-17α-
pregna-4-en-3-one-21-carboxylic acid γ-lactone
17β-Hydroxy-7β-ethyl-18-methyl-15α,16α-methylene-19-nor-17α-
pregna-4-en-3-one-21-carboxylic acid γ-lactone

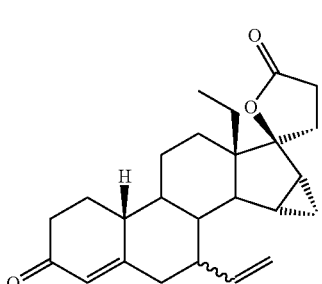

17β-Hydroxy-7α-vinyl-18-methyl-15α,16α-methylene-19-nor-17α-
pregna-4-en-3-one-21-carboxylic acid γ-lactone
17β-Hydroxy-7β-vinyl-18-methyl-15α,16α-methylene-19-nor-17α-
pregna-4-en-3-one-21-carboxylic acid γ-lactone

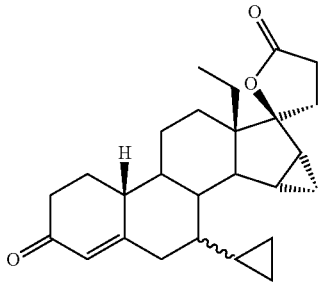

17β-Hydroxy-7α-cyclopropyl-18-methyl-15α,16α-methylene-19-nor-
17α-pregna-4-en-3-one-21-carboxylic acid γ-lactone
17β-Hydroxy-7β-cyclopropyl-18-methyl-15α,16α-methylene-19-nor-
17α-pregna-4-en-3-one-21-carboxylic acid γ-lactone

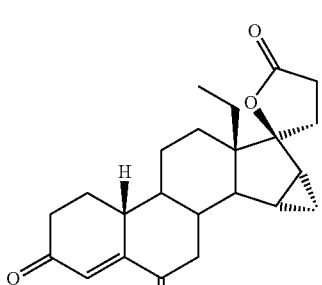

17β-Hydroxy-6-methylene-18-methyl-15α,16α-methylene-19-nor-17α-
pregna-4-en-3-one-21-carboxylic acid γ-lactone -continued

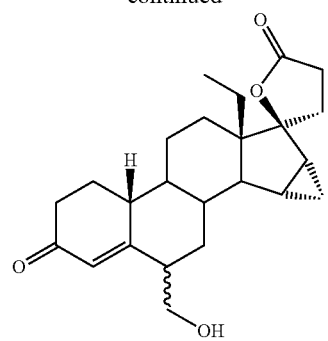

17β-Hydroxy-6α-hydroxymethyl-18-methyl-15α,16α-methylene-19-nor-17α-pregna-4-en-3-one-21-carboxylic acid γ-lactone
17β-Hydroxy-6β-hydroxymethyl-18-methyl-15α,16α-methylene-19-nor-17α-pregna-4-en-3-one-21-carboxylic acid γ-lactone

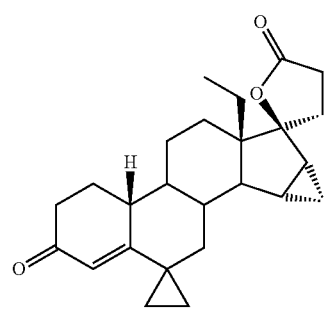

6,6-(1,2-Ethanediyl)-17β-hydroxy-18-methyl-15α,16α-methylene-19-nor-17α-pregna-4-en-3-one-21-carboxylic acid γ-lactone

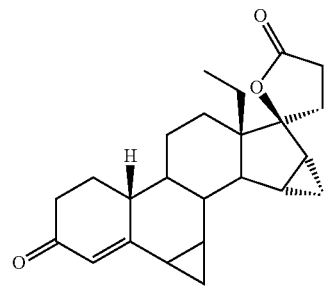

17β-Hydroxy-6α,7α,15α,16α-bismethylene-19-nor-17α-pregna-4-en-3-one-21-carboxylic acid γ-lactone
17β-Hydroxy-6β,7β,15α,16α-bismethylene-19-nor-17α-pregna-4-en-3-one-21-carboxylic acid γ-lactone

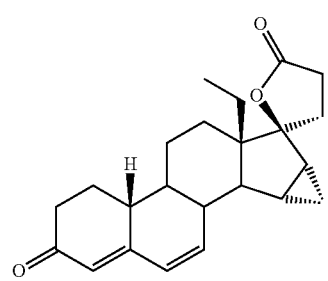

17β-Hydroxy-18-methyl-15α,16α-methylene-19-nor-17α-pregna-4,6-dien-3-one-21-carboxylic acid γ-lactone -continued

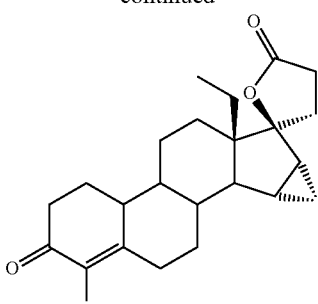

4-Chloro-17β-hydroxy-15α,16α-methylene-19-nor-17α-pregna-4-en-3-one-21-carboxylic acid γ-lactone

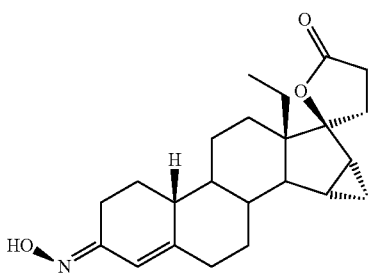

(E/Z)-3-(Hydroxyimino)-17β-hydroxy-18-methyl-15α,16α-methylene-19-nor-17α-pregna-4-ene-21-carboxylic acid γ-lactone

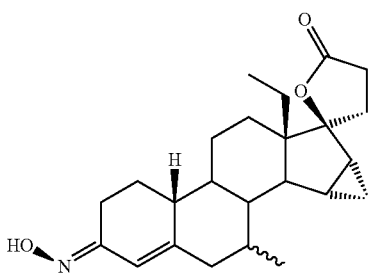

(E/Z)-3-(Hydroxyimino)-17β-hydroxy-7α-methyl-18-methyl-15α,16α-methylene-19-nor-17α-pregna-4-ene-21-carboxylic acid γ-lactone
(E/Z)-3-(Hydroxyimino)-17β-hydroxy-7β-methyl-18-methyl-15α,16α-methylene-19-nor-17α-pregna-4-ene-21-carboxylic acid γ-lactone

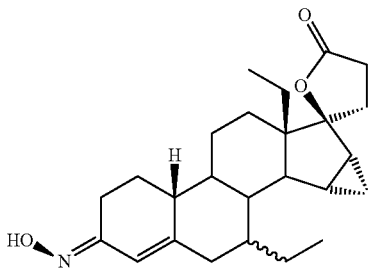

(E/Z)-3-(Hydroxyimino)-17β-hydroxy-7α-ethyl-18-methyl-15α,16α-methylene-19-nor-17α-pregna-4-ene-21-carboxylic acid γ-lactone
(E/Z)-3-(Hydroxyimino)-17β-hydroxy-7β-ethyl-18-methyl-15α,16α-methylene-19-nor-17α-pregna-4-ene-21-carboxylic acid γ-lactone -continued

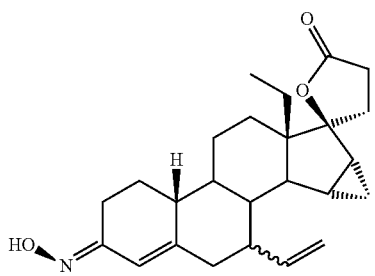

(E/Z)-3-(Hydroxyimino)-17β-hydroxy-7α-vinyl-18-methyl-15α,16α-methylene-19-nor-17α-pregna-4-ene-21-carboxylic acid γ-lactone
(E/Z)-3-(Hydroxyimino)-17β-hydroxy-7β-vinyl-18-methyl-15α,16α-methylene-19-nor-17α-pregna-4-ene-21-carboxylic acid γ-lactone

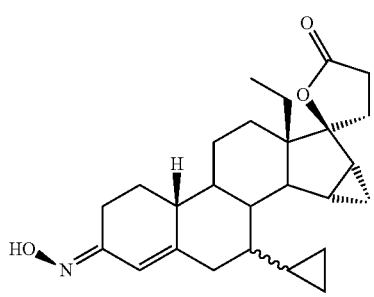

(E/Z)-3-(Hydroxyimino)-17β-hydroxy-7α-cyclopropyl-18-methyl-15α,16α-methylene-19-nor-17α-pregna-4-ene-21-carboxylic acid γ-lactone
(E/Z)-3-(Hydroxyimino)-17β-hydroxy-7β-cyclopropyl-18-methyl-15α,16α-methylene-19-nor-17α-pregna-4-ene-21-carboxylic acid γ-lactone

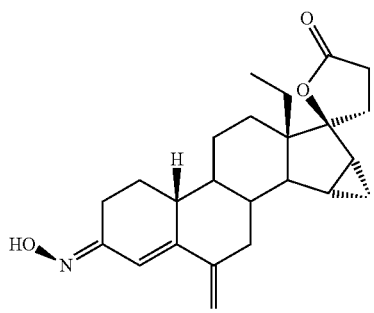

(E/Z)-3-(Hydroxyimino)-17β-hydroxy-6-methylene-18-methyl-15α,16α-methylene-19-nor-17α-pregna-4-ene-21-carboxylic acid γ-lactone

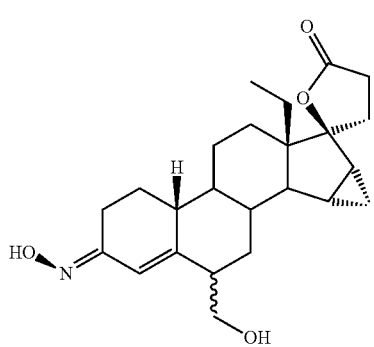

(E/Z)-3-(Hydroxyimino)-17β-hydroxy-6α-hydroxymethyl-18-methyl-15α,16α-methylene-19-nor-17α-pregna-4-ene-21-carboxylic acid γ-lactone
(E/Z)-3-(Hydroxyimino)-17β-hydroxy-6β-hydroxymethyl-18-methyl-15α,16α-methylene-19-nor-17α-pregna-4-ene-21-carboxylic acid γ-lactone -continued

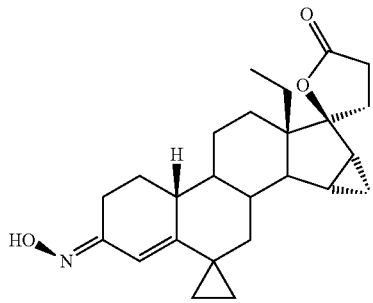

(E/Z)-3-(Hydroxyimino)-6,6-(1,2-ethanediyl)-17β-hydroxy-18-methyl-15α,16α-methylene-19-nor-17α-pregna-4-ene-21-carboxylic acid γ-lactone

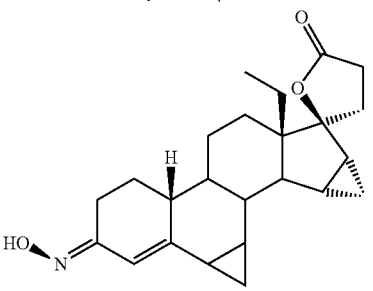

(E/Z)-3-(Hydroxyimino)-17β-hydroxy-6α,7α,15α,16α-bismethylene-19-nor-17α-pregna-4-ene-21-carboxylic acid γ-lactone
(E/Z)-3-(Hydroxyimino)-17β-hydroxy-6β,7β,15α,16α-bismethylene-19-nor-17α-pregna-4-ene-21-carboxylic acid γ-lactone

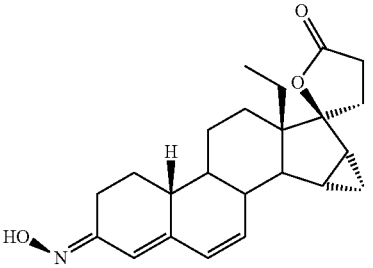

(E/Z)-3-(Hydroxyimino)-17β-hydroxy-18-methyl-15α,16α-methylene-19-nor-17α-pregna-4,6-diene-21-carboxylic acid γ-lactone

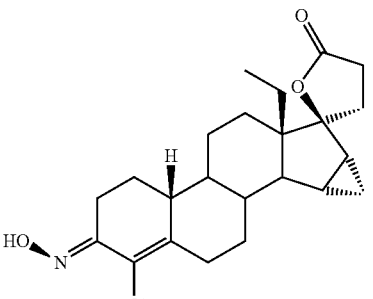

(E/Z)-3-(Hydroxyimino)-4-chloro-17β-hydroxy-18-methyl-15α,16α-methylene-19-nor-17α-pregna-4-ene-21-carboxylic acid γ-lactone On the basis of their progestational efficacy, the novel compounds with the general chemical formula I can be used alone or in combination with estrogen in medicinal products for contraception.

The derivatives according to the invention are therefore suitable in particular for the production of a medicinal product for oral contraception and for the treatment of pre-, periand postmenopausal complaints, including use in preparations for hormone replacement therapy (HRT).

Owing to their favorable action profile, the derivatives according to the invention are moreover especially well suited to the treatment of premenstrual complaints, such as headaches, depressive moods, water retention and mastodynia.

The use of the derivatives according to the invention is especially preferred for the production of a medicinal product with progestational, and preferably also antimineralocorticoid and neutral to slightly androgenic action.

Treatment with the derivatives according to the invention is preferably applied to humans, but can also be carried out on related mammalian species, for example dog and cat.

For use of the derivatives according to the invention as medicinal products, they are combined with at least one suitable pharmaceutically harmless additive, for example a carrier. The additive is for example suitable for parenteral, preferably oral, application. Relevant materials are pharmaceutically suitable organic or inorganic inert additives, for example water, gelatin, gum arabic, lactose, starch, magnesium stearate, talc, vegetable oils, polyalkylene glycols etc. The medicinal products can be in solid form, for example as tablets, coated tablets, suppositories, capsules, or in liquid form, for example as solutions, suspensions or emulsions. Optionally they also contain excipients, such as preservatives, stabilizers, wetting agents or emulsifiers, salts for altering the osmotic pressure or buffers. For parenteral application, oily solutions are suitable in particular, for example solutions in sesame oil, castor oil and cottonseed oil. To increase the solubility, solubilizers can be added, for example benzyl benzoate or benzyl alcohol. It is also possible to incorporate the derivatives according to the invention in a transdermal system and therefore apply them transdermally. For oral application, consideration may be given in particular to tablets, coated tablets, capsules, pills, suspensions or solutions.

Further examples of administration routes are intravaginal or intrauterine administration. This is possible with physiologically tolerated solutions such as, for example, an aqueous or oily solution with or without suitable solubilizers, dispersants or emulsifiers. Examples of suitable oils are peanut oil, cottonseed oil, castor oil or sesame oil. The selection is by no means restricted thereto.

For intravaginal or intrauterine administration it is possible to use special systems such as an intravaginal system (e.g. vaginal ring, VRS) or an intrauterine system (IUS) which release an active substance of the present invention from a reservoir over a prolonged period (e.g. 1, 2, 3, 4 or 5 years).

A representative example of an intrauterine system which may be mentioned is MIRENA®. This is a T-shaped, levonorgestrel-releasing intrauterine system from Bayer Schering Pharma AG.

Administration is further possible via an implanted depot system composed of an inert carrier material such as, for example, a biodegradable polymer or a synthetic silicone polymer. These depot systems release the active ingredient in a controlled manner over a prolonged period (e.g. 3 months to 3 years) and are implanted subcutaneously.

The dosage of the derivatives according to the invention in contraceptive preparations should be 0.01 to 10 mg per day. The daily dose in the treatment of premenstrual complaints is around 0.1 to 20 mg. The progestational derivatives according to the invention are preferably administered orally in contraceptive preparations and in medicinal products for the treatment of premenstrual complaints. The daily dose is preferably administered as a single dose. The aforementioned dosages relate to oral administration forms.

On use of a depot formulation, the appropriate dosage, equivalent to the aforementioned oral dosages, is released continuously each day from the depot systems described above and employed in the long term.

A depot formulation, for example an IUS, releases per day an amount of 0.005 to 10 mg of a compound of general formula 1.

The progestational and estrogenic active components are preferably applied together orally in contraceptive preparations. The daily dose is preferably administered as a single dose.

As estrogens, consideration may be given to synthetic estrogens, preferably ethinylestradiol, but also mestranol, and natural estrogens, including phytoestrogens.

The estrogen is administered in a daily amount that corresponds to the pharmacological action of 0.01 to 0.04 mg ethinylestradiol. This amount relates to an oral administration form. If a different administration route is chosen, an appropriate dosage amount equivalent to the aforementioned oral dosage is to be used.

As estrogens in medicinal products for the treatment of pre-, perk and postmenopausal complaints and for hormone replacement therapy, natural estrogens are mainly used, in particular estradiol, but also the esters of estradiol, for example estradiol valerate, or also conjugated estrogens (CEEs=conjugated equine estrogens).

The progestational, antimineralocorticoid and androgenic or antiandrogenic action of the compounds according to the invention was investigated by the following methods:

1. Progesterone Receptor Binding Test:

Using cytosol from progesterone receptor-expressing insect cells (Hi5), competitive binding to the progesterone receptor was determined from the ability to displace $^3$H-progesterone as reference substance from the receptor. If a compound has an affinity corresponding to progesterone, this corresponds to a competition factor (CF) of 1. CF values greater than 1 are characterized by a lower affinity for the progesterone receptor, and CF values of less than 1 are characterized by higher affinity.

2. Mineralocorticoid Receptor Binding Test:

The test was carried out as in 1., with the following modifications: cytosol from mineralocorticoid receptor-expressing insect cells (Hi5) was used, and the reference substance was $^3$H-aldosterone.

3. Androgen Receptor Binding Test:

The test was carried out as in 1, with the following modifications: cytosol from androgen receptor-expressing insect cells (Hi5) was used, and the reference substance was $^3$H-testosterone.

The results of the binding tests and the ratio of the competition factors CF(PR) and CR(MR) are shown in Table 1, which for comparison also shows receptor binding values of drospirenone as reference substance A.

4. Determination of Progestational Action by Means of Transactivation Tests:

The culture medium used for culture of the cells used for the assay was DMEM (Dulbecco's Modified Eagle Medium: 4500 mg/ml glucose; PAA, #E15-009) with 10% FCS (Biochrom, S0115, batch #615B), 4 mM L-glutamine, 1% penicillin/streptomycin, 1 mg/ml G418 and 0.5 µg/ml puromycin.

Reporter cell lines (CHO K1 cells stably transfected with a fusion protein from the PR-ligand-binding domain and a Gal4-transactivation domain and a reporter construct, which contained luciferase under the control of a Gal4-responsive promoter) were seeded at a density of $4\times10^4$ cells per well in white, opaque tissue culture plates each with 96 wells (Perkin Elmer, #P12-106-017) and kept in culture medium with 3%

DCC-FCS (serum treated with activated charcoal to remove interfering components contained in the serum). The test compounds were added eight hours later, and the cells were incubated with the compounds for 16 hours. The tests were carried out in triplicate. At the end of incubation the medium containing the effector was removed and replaced with lysis buffer. After luciferase assay substrate (Promega, #E1501) had been added, the 96-well plates were then put in a microplate luminometer (Pherastar, BMG labtech), and the luminescence was measured. The $IC_{50}$ values were evaluated using software for calculating dose-effect relations. Table 1 presents the test results and, for comparison, corresponding results for drospirenone as reference substance A.

If the production of the starting compounds is not described here, these are known to a person skilled in the art or can be prepared similarly to known compounds or methods described here. The isomeric mixtures can be separated into the individual compounds by the usual methods, for example crystallization, chromatography or salt formation. The salts are prepared in the usual way, by adding, to a solution of the compounds with the general chemical formula I, the equivalent amount or an excess of a base or acid, which is optionally in solution, if necessary separating the precipitate or processing the solution in the usual way.

The compounds of general formula I are prepared, starting from compounds of general formula 1 (Scheme 2), according to the methods shown in Scheme 1, in which $R^4$, $R^{6a}$, $R^{6b}$, $R^7$, $R^{18}$ and Z have the meanings stated previously and $R^6$, $R^7$ in 5 and 6, together denote an oxygen or a methylene group, U denotes an oxygen atom, two alkoxy groups $OR^{19}$, a $C_2$-$C_{10}$-alkylene-dioxy group, which can be linear or branched, and $R^{19}$ stands for a $C_1$-$C_{20}$-alkyl residue, $R^{20}$ denotes a $C_1$-$C_{20}$-alkyl residue, X denotes an $NR^{21a}R^{21b}$ group, an alkoxy group $OR^{22}$ $R^{21a}$, $R^{21b}$ which may be identical or different, denote hydrogen, $C_1$-$C_{10}$-alkyl or together a $C_4$-$C_{10}$—-alkylene group, which can be linear or branched, $R^{22}$ denotes a $C_1$-$C_{20}$-alkyl residue.

Compounds 2 and 3 in Scheme 1 each have a double bond between C5 and C6 or C5 and C10 and another double bond between C2 and C3 or C3 and C4.

Compounds 7 to 9 in Scheme 1 each have a double bond between C4 and C5 or C5 and C6 or C5 and C10.

For a person skilled in the art it is obvious that in the descriptions of the synthetic transformations it is always assumed that if necessary other functional groups present on the steroid structure are suitably protected.

The introduction of a 6,7-double bond with formation of compounds with the general chemical formulae 4, 13 or 18 is carried out by bromination of the respective 3,5-dienol ethers 3, 12 or 17 followed by elimination of hydrogen bromide (see for example J. Fried, J. A. Edwards, Organic Reactions in Steroid Chemistry, Van Nostrand Reinhold Company 1972, p. 265-374).

The dienol ether bromination of compounds 3, 12 or 17 can for example be carried out as for the specification from Steroids 1, 233 (1963). Hydrogen bromide elimination with formation of the compounds with the general chemical formulae 4, 13 or 18 is achieved by heating the 6-bromo compound with basic reagents, for example with LiBr or $Li_2CO_3$, in aprotic solvents, such as dimethylformamide, at temperatures of 50-120° C. or alternatively by heating the 6-bromo compounds in a solvent, such as collidine or lutidine.

The introduction of a substituent $R^4$ can be carried out, for example, starting from a compound of formula 6, 11, 13, 14, 16 or 18, by epoxidation of the 4,5-double bond with hydrogen peroxide under alkaline conditions and reaction of the resultant epoxides in a suitable solvent with acids with the general formula H—$R^4$, where $R^4$ can be a halogen atom, preferably chlorine or bromine. Compounds in which $R^4$ has the meaning bromine can for example be reacted with methyl 2,2-difluoro-2-(fluorosulfonyl)acetate in dimethylformamide in the presence of copper(I) iodide to compounds in which $R^4$ has the meaning fluorine. Alternatively, starting from a compound of formula 6, 11, 13, 14, 16 or 18, halogen can be introduced directly by reaction with sulfuryl chloride or sulfuryl bromide in the presence of a suitable base, for example pyridine, with $R^4$ having the meaning chlorine or bromine.

Compound 4 is converted by methenylation of the 6,7-double bond by known methods, for example with dimethylsulfoxonium methylide (see for example DE-A 11 83 500, DE-A 29 22 500, EP-A 0 019 690, U.S. Pat. No. 4,291,029; J. Am. Chem. Soc. 84, 867 (1962)) to a compound 5 ($R^6$, $R^7$ together form a methylene group), obtaining a mixture of the α- and β-isomers, which can be separated into the individual isomers for example by chromatography.

Compounds of type 5 can be obtained as described in the examples or similarly to these specifications, using similar reagents to those described there.

Synthesis of the spirocyclic compound 18 ($R^{6a}$, $R^{6b}$ together form 1,2-ethanediyl) starts from compounds 11 or 14, which are first converted to a 3-amino-3,5-diene derivative 15 (X=$NR^{21a}R^{21b}$). By reaction with formalin in alcoholic solution, the 6-hydroxymethylene derivative 16 ($R^6$=hydroxymethylene) is obtained. After converting the hydroxyl group into a leaving group, such as a mesylate, tosylate or even benzoate, compound 18 can be prepared by reaction with trimethylsulfoxonium iodide using bases, such as alkali hydroxides, alkali alcoholates in suitable solvents such as dimethyl sulfoxide.

For introduction of a 6-methylene group, compound 16 ($R^6$=hydroxymethylene) can be dehydrated with for example hydrochloric acid in dioxane/water. Compound 18 ($R^{6a}$, $R^{6b}$ together form methylene) can also be produced after converting the hydroxyl group into a leaving group, such as a mesylate, tosylate or even benzoate (see DE-A 34 02 3291, EP-A. 0 150 157, U.S. Pat. No. 4,584,288; J. Med. Chem. 34, 2464 (1991)).

Another possibility for the production of 6-methylene compounds 18 is the direct reaction of the 4(5)-unsaturated 3-ketones such as compound 16 ($R^6$=hydrogen), with formaldehyde acetals in the presence of sodium acetate with for example phosphorus oxychloride or phosphorus pentachloride in suitable solvents such as chloroform (see for example K. Annen, H. Hofineister, H. Laurent and R. Wiechert, Synthesis 34 (1982)).

The 6-methylene compounds can be used for the preparation of compounds of general formula 18, in which $R^{6a}$ is methyl and $R^{6b}$ and $R^7$ together form an additional bond.

For this it is possible for example to use a method described in Tetrahedron 21, 1619 (1965), in which isomerization of the double bond is achieved by heating the 6-methylene compounds in ethanol with 5% palladium/charcoal catalyst, which has been pretreated either with hydrogen or by heating with a small amount of cyclohexene. The isomerization can also be carried out with a catalyst that has not been pretreated, if a small amount of cyclohexene is added to the reaction mixture. The formation of small proportions of hydrogenated products can be prevented by adding an excess of sodium acetate.

Alternatively, compound 17 (X=OR$^{22}$) can be used as precursor. The direct preparation of 6-methyl-4,6-dien-3-one derivatives has been described (see K. Annen, H. Hofineister, H. Laurent and R. Wiechert, Lieb. Ann. 712 (1983)).

Compounds 18 in which R$^{6b}$ represents an α-methyl function can be prepared in suitable conditions from the 6-methylene compounds (18: R$^{6a}$, R$^{6b}$ together form methylene) by hydrogenation under suitable conditions. The best results (selective hydrogenation of the exo-methylene function) are achieved by transfer-hydrogenation (J. Chem. Soc. 3578 (1954)). If the 6-methylene derivatives 18 are heated in a suitable solvent, for example ethanol, in the presence of a hydride donor, for example cyclohexene, then 6α-methyl derivatives are obtained at very good yields. Small proportions of 6β-methyl compound can be isomerized in acid conditions (Tetrahedron 1619 (1965)).

The selective preparation of 6β-methyl compounds is also possible. For this, the 4-en-3-ones such as compound 16 are reacted for example with ethylene glycol, trimethyl orthoformate in dichloromethane in the presence of catalytic amounts of an acid, for example p-toluenesulfonic acid, to the corresponding 3-ketals. During this ketalization there is isomerisation of the double bond into position 5. Selective epoxidation of this 5-double bond is achieved for example by using organic per-acids, for example m-chloroperbenzoic acid, in suitable solvents such as dichloromethane. As an alternative, the epoxidation can also be carried out with hydrogen peroxide in the presence of for example hexachloroacetone or 3-nitrotrifluoroacetophenone. The 5,6α-epoxides formed can then be opened axially using appropriate alkylmagnesium halides or alkyllithium compounds. In this way, 5α-hydroxy-6β-alkyl compounds are obtained. The 3-keto protecting group can be cleaved, obtaining the 5α-hydroxy function, by treatment in mild acidic conditions (acetic acid or 4N hydrochloric acid at 0° C.). Basic elimination of the 5α-hydroxy function with for example dilute aqueous sodium hydroxide solution yields the 3-keto-4-ene compounds with a 6-alkyl group in the β position. Alternatively, cleavage of the ketal in harsher conditions (aqueous hydrochloric acid or another strong acid) yields the corresponding 6α-alkyl compounds.

The introduction of a 7-alkyl, 7-alkenyl or 7-alkynyl group to compounds of general formula 14 is effected by 1,6-addition of a corresponding organometallic compound to the precursor of general formula 13 under the action of copper salts. Divalent metals, such as magnesium and zinc, are preferred; chlorine, bromine and iodine are preferred as counter ion. Suitable copper salts are monovalent or divalent copper compounds, for example copper chloride, copper bromide or copper acetate. The reaction takes place in an inert solvent, for example tetrahydrofuran, diethyl ether or dichloromethane.

The compounds 6, 11, 13, 14, 16, 18 or 20 obtained, in which Z stands for an oxygen atom, can be converted by reaction with hydroxylamine hydrochloride, alkyloxyamine hydrochlorides or sulfonyl hydrazines in the presence of a tertiary amine at temperatures between −20 and +40° C. to their corresponding E/Z-configured oximes or sulfonyl hydrazones (general formula I with Z denoting =NOR$^1$, =NNHSO$_2$R$^1$)). Suitable tertiary bases are for example trimethylamine, triethylamine, pyridine, N,N-dimethylaminopyridine, 1,5-diazabicyclo[4.3.0]non-5-ene (DBN) and 1,5-diazabicyclo[5.4.0]undec-5-ene (DBU), pyridine being preferred. An analogous method is described for example in WO 98/24801 for the production of corresponding 3-oxyimino derivatives of drospirenone.

For the preparation of an end product with the general chemical formula I with Z denoting two hydrogen atoms, the 3-oxo group can be removed for example following the instructions given in DE-A 28 05 490 by reductive cleavage of a thioketal of the 3-keto compound on a suitable precursor, for example compounds of the general formulae 6, 11, 13, 14, 16, 18 or 20.

The formation of spirolactones to compounds of the general formulae 6 or 11 is carried out starting from the corresponding 17-hydroxypropenyl compounds 5 or 10, by oxidation. Oxidation processes that may be mentioned are for example the Jones oxidation, oxidation with potassium permanganate for example in an aqueous system of tert.-butanol and sodium dihydrogen phosphate, oxidation with sodium chlorite in aqueous tert.-butanol, optionally in the presence of a chlorine trap, for example 2-methyl-2-butene, or by oxidation with manganese dioxide.

Alternatively the spirolactone can be introduced directly from the ketones of general formulae 1 or 7 optionally also after cleavage of the enol ethers in 1 or ketals in 7 according to the method described by Georges Sturtz et al. in Tetrahedron Letters 47 (1976).

Scheme 1

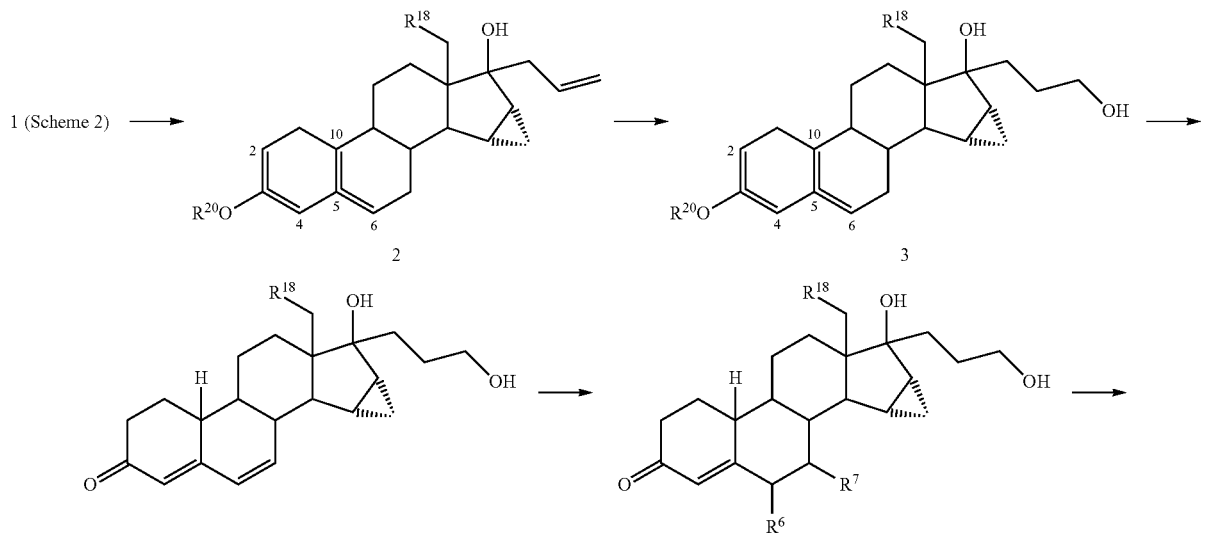

-continued
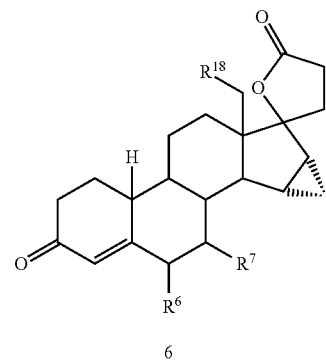
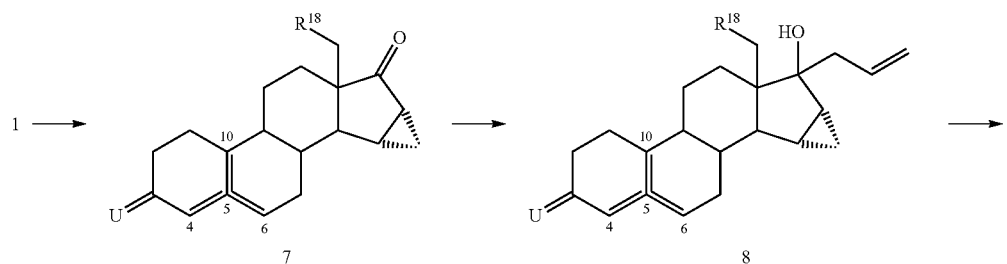
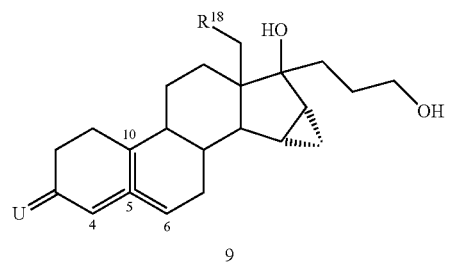
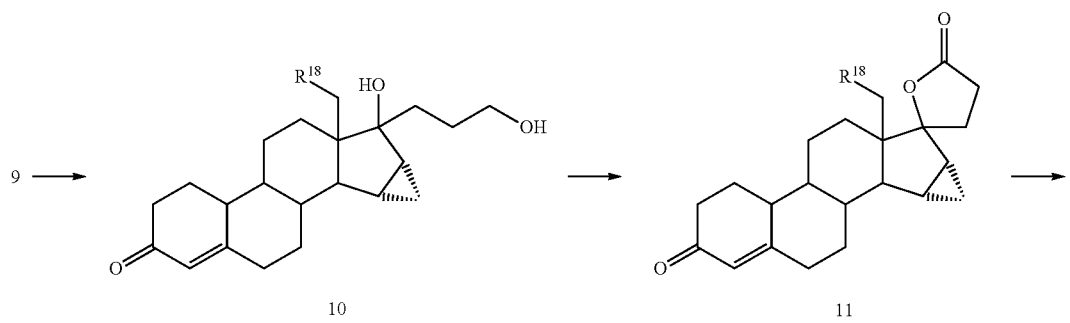
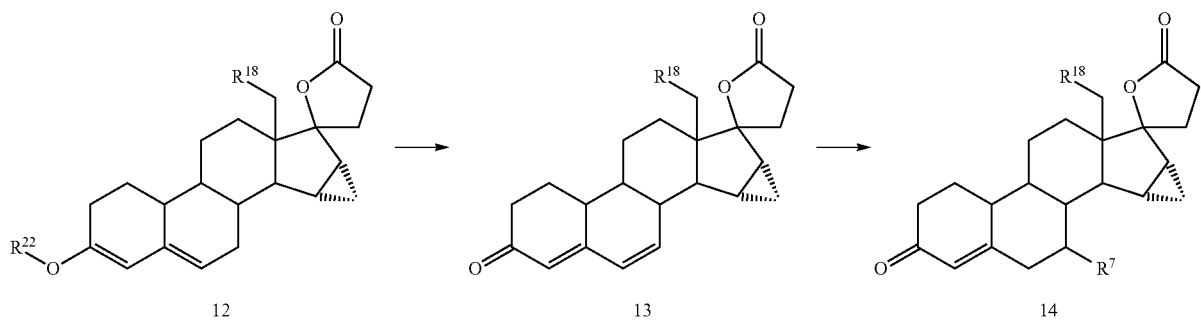

-continued
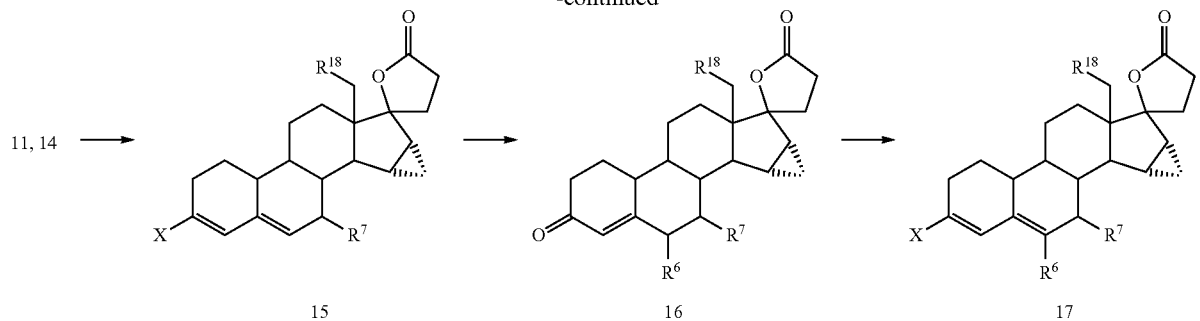
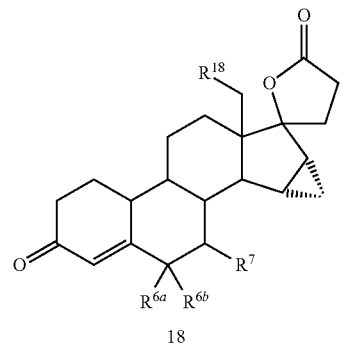
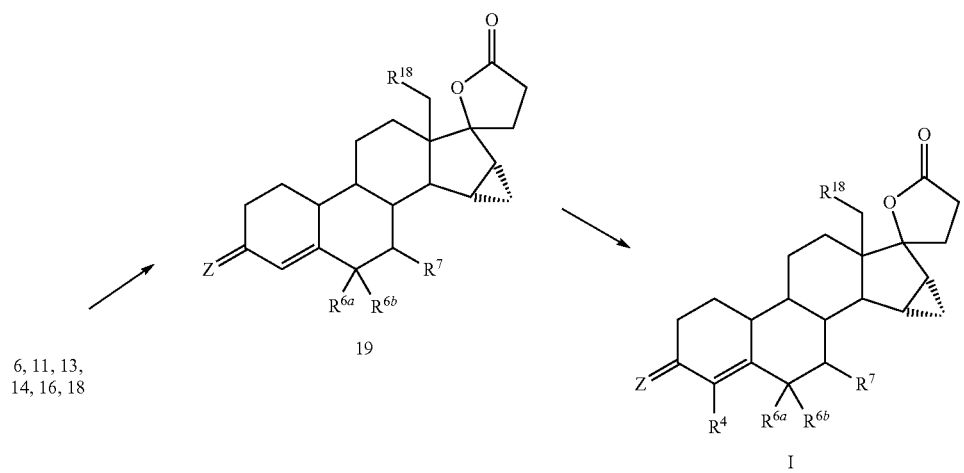
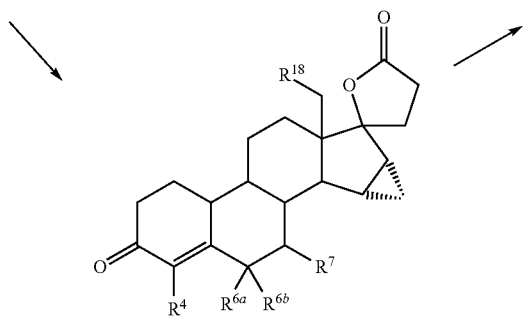

Compound 1 in Scheme 2 in each case has a double bond between C5 and C6 or C5 and C10 and another double bond between C2 and C3 or C3 and C4.

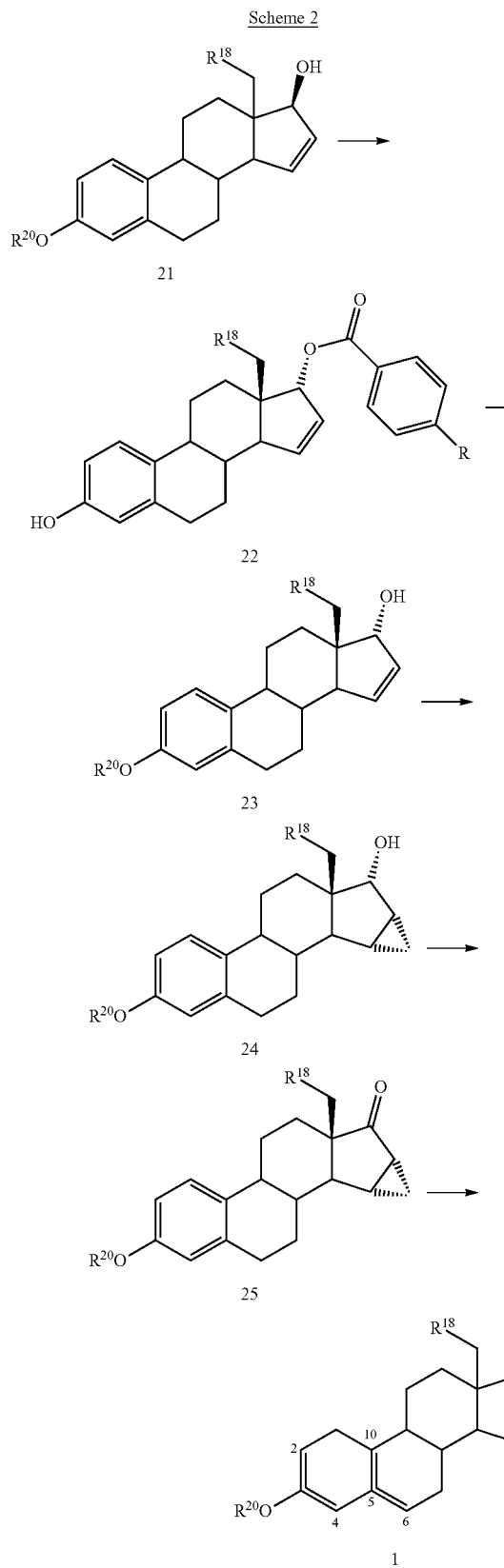

Scheme 2

The following examples offer a more detailed explanation of the invention without limiting it to these examples:

EXAMPLE 1

17-Spirolactonization with Manganese Dioxide

17β-Hydroxy-15α,16α-methylene-19-nor-17α-pregna-4-en-3-one-21-carboxylic acid γ-lactone

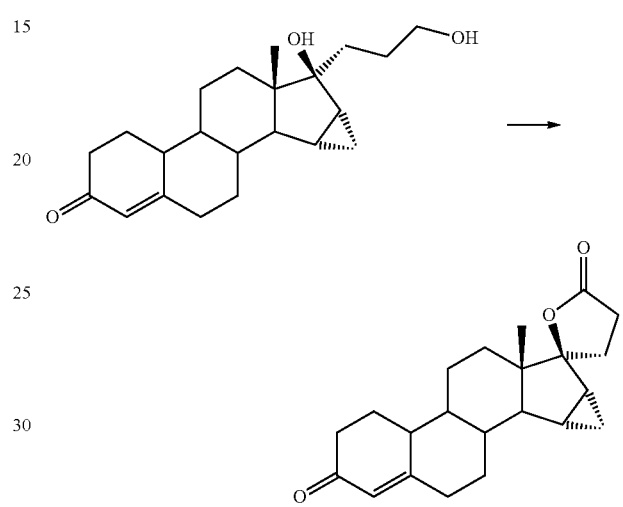

1.14 g manganese dioxide is added to a solution of 150 mg of the compound prepared according to Example 1a in 7 ml dichloromethane and it is stirred for approx. 16 hours at 23° C. It is filtered on Celite and after concentration by evaporation and chromatography, 125 mg of the title compound is isolated.

$^1$H-NMR (CDCl$_3$): δ=0.52 (1H), 0.57 (1H), 0.75 (1H), 1.03 (1H), 1.15 (1H), 1.22 (3H), 1.23-134 (3H), 1.43-1.65 (3H), 1.76-1.86 (2H), 1.97-2.56 (11H), 5.84 (1H) ppm.

EXAMPLE 1a

Cleavage of 3-ketal

17α(Z)-(3'-Hydroxyprop-1'-yl)-15α,16α-methylene-17β-hydroxyestra-4-en-3-one

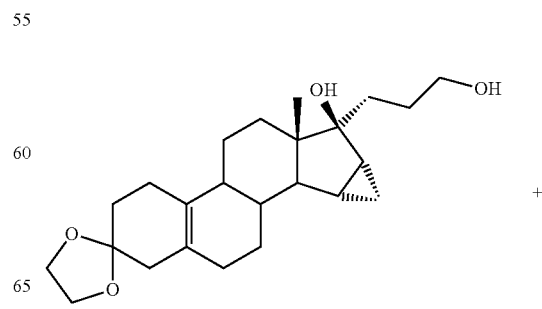

+

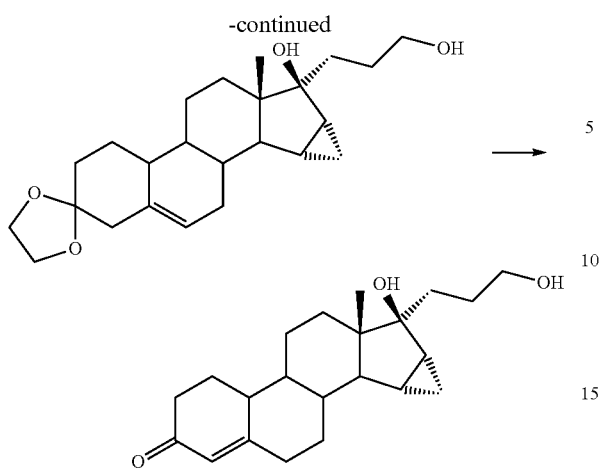

1.8 μl of 4N hydrochloric acid is added to a solution of 880 mg of the compounds prepared according to Example 1b in 35 ml acetone and it is stirred for 1 hour at 23° C. It is poured into saturated sodium hydrogencarbonate solution, extracted several times with ethyl acetate, the combined organic extracts are washed with saturated sodium chloride solution and dried over sodium sulfate. The residue obtained after filtration and evaporation of the solvent is purified by chromatography. 580 mg of the title compound is isolated.

EXAMPLE 1b

Hydroboration

17α(Z)-(3'-Hydroxyprop-1'-yl)-15α,16α-methylene-17β-hydroxyestra-5-en-3-one-3-ethylene ketal and 17α(Z)-(3'-hydroxyprop-1'-yl)-15α,16α-methylene-17β-hydroxyestra-5(10)-en-3-one-3-ethylene ketal

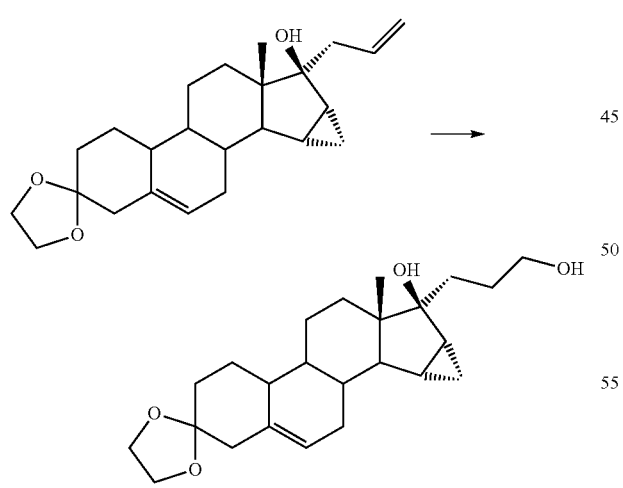

10.5 ml of a 0.5-molar solution of 9-borabicyclononane in tetrahydrofuran is added to a solution of 643 mg of the compound prepared according to Example 1c in 7.5 ml tetrahydrofuran and it is stirred for 4 hours at 23° C. It is cooled to 4° C., 4.6 ml of 5% sodium hydroxide solution and 1.2 ml of 30% hydrogen peroxide solution are added and it is stirred for a further 15 hours at 23° C. It is extracted with ethyl acetate, the combined organic extracts are washed with water, saturated sodium thiosulfate solution, and saturated sodium chloride solution and dried over sodium sulfate. After filtration and removal of the solvent, 880 mg of the title compound is isolated, and is reacted further without purification.

EXAMPLE 1c 17-allyl Addition

17α-(2'-Propen-1'-yl)-15α,16α-methylene-17β-hydroxyestra-5-en-3-one-3-ethylene ketal and 17α-(2'-propen-1'-yl)-15α,16α-methylene-17β-hydroxyestra-5(10)-en-3-one-3-ethylene ketal

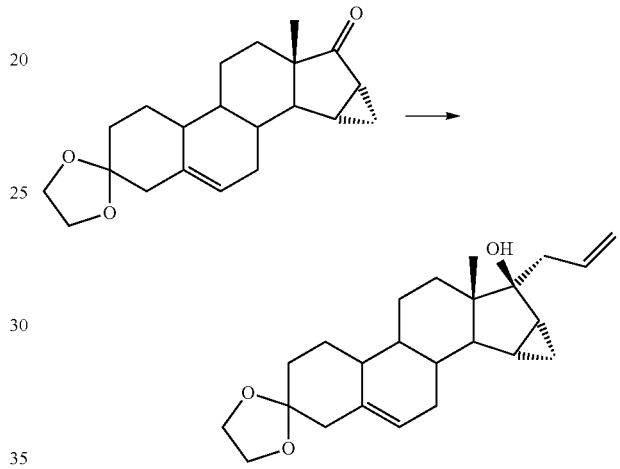

4.38 ml of a 1-molar solution of allylmagnesium bromide in diethyl ether is added at 4° C. to a solution of 600 mg of the compound prepared according to Example 1d in 10 ml dichloromethane, stirred for 1 minute and poured into saturated ammonium chloride solution. It is extracted with ethyl acetate, the combined organic extracts are washed with saturated sodium chloride solution and dried over sodium sulfate. After filtration and removal of the solvent, 690 mg of the title compound is isolated, and is reacted further without purification.

EXAMPLE 1d

Oxidation of 17-OH

15α,16α-Methylene-estra-5-ene-3,17-dione-3-ethylene ketal and 15α,16α-methylene-estra-5(10)-ene-3,17-dione-3-ethylene ketal

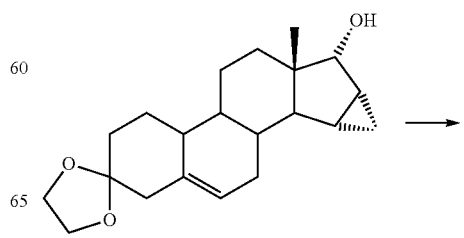

-continued

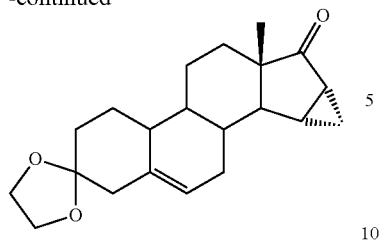

A spatula tip of molecular sieve 4A, 700 mg N-methylmorpholino-N-oxide, and 90 mg tetrabutylammonium perruthenate are added to a solution of 1.06 g of the compound prepared according to Example 1e in 32 ml dichloromethane and it is stirred at 23° C. for approx. 16 hours. It is concentrated by evaporation and the residue is purified by chromatography. 878 mg of the title compounds is isolated.

EXAMPLE 1e 3-enol ether to ethylene ketal

15α,16α-Methylene-17α-hydroxyestra-5-en-3-one-3-ethylene ketal and 15α,16α-methylene-17α-hydroxyestra-5(10)-en-3-one-3-ethylene ketal

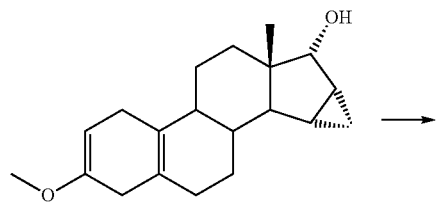

10 ml ethylene glycol and 4.4 mg p-toluenesulfonic acid hydrate are added to a solution of 500 mg of the compound prepared according to Example 1f in 10 ml tetrahydrofuran and it is stirred at 23° C. for 2 hours. It is poured into saturated sodium hydrogencarbonate solution, extracted several times with ethyl acetate, the combined organic extracts are washed with saturated sodium chloride solution and dried over sodium sulfate. The residue obtained after filtration and evaporation of the solvent is purified by chromatography. 359 mg of the title compound is isolated.

EXAMPLE 1f (Birch) 3-Methoxy-15α,16α-methylene-17α-hydroxyestra-2,5(10)-diene

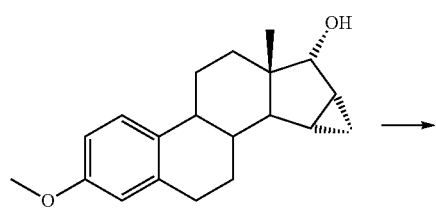

-continued

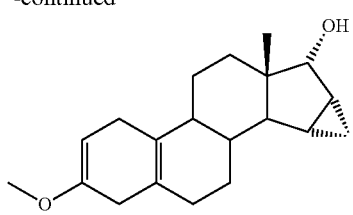

9.91 g lithium is added to 597 ml ammonia at −75° C. and within 1 hour a solution of 24.6 g of the compound prepared according to Example 1g in 1.2 l tetrahydrofuran is added dropwise. 720 ml ethanol is added, after 1 hour it is allowed to warm up to −50° C. and it is stirred for a further 2 hours. Then 600 ml water is added, it is allowed to warm up to 23° C., it is extracted several times with ethyl acetate, the combined organic extracts are washed with saturated sodium chloride solution and dried over sodium sulfate. After filtration and removal of the solvent, 27.1 g of the title compound is isolated, and is reacted further without purification.

EXAMPLE 1g

Simmons Smith

3-Methoxy-15α,16α-methylene-17α-hydroxyestra-1,3,5(10)-triene

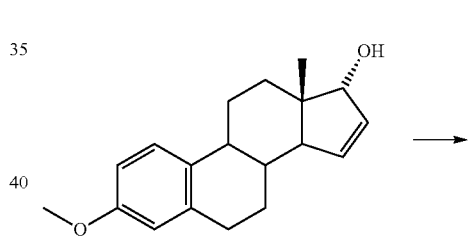

86.6 g zinc dust is added to a suspension of 1.5 g copper(II) acetate in 900 ml diethyl ether and it is heated under reflux for 10 minutes. Then 11.7 ml diiodomethane is added, and it is heated under reflux for a further 30 minutes. A solution of 37.6 g of the compound prepared according to Example 1h in 100 ml tetrahydrofuran is added and, spread over a total of 40 hours, a further 35 ml of diiodomethane is added. The cooled mixture is filtered on Celite, the filtrate is washed with saturated sodium chloride solution and dried over sodium sulfate. The residue obtained after filtration and evaporation of the solvent is purified by recrystallization. 24.6 g of the title compound is isolated.

EXAMPLE 1h

Benzoate Saponification

3-Methoxy-17α-hydroxyestra-1,3,5(10),15-tetraene

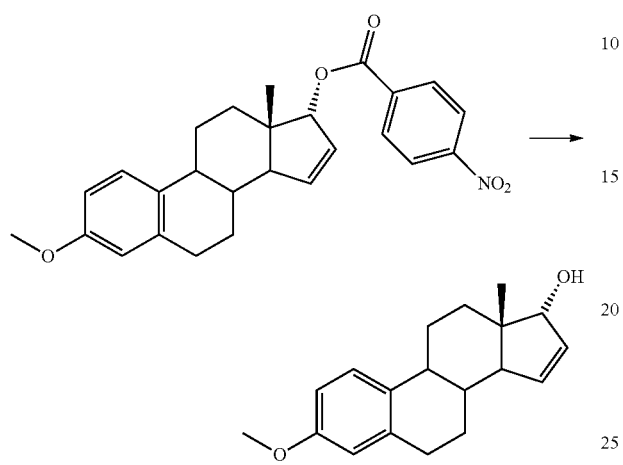

75.5 g potassium carbonate is added to a solution of 96.3 g of the compound prepared according to Example 1i in 1.1 l methanol and it is stirred at 50° C. for 2 hours. It is concentrated by evaporation, water is added, it is extracted several times with ethyl acetate, the combined organic extracts are washed with water and dried over sodium sulfate. The residue obtained after filtration and evaporation of the solvent is purified by recrystallization. 46 g of the title compound is isolated.

EXAMPLE 1i

Mitsunobu

4-Nitro-benzoic acid 3-methoxy-estra-1,3,5(10),15-tetraen-17-yl ester

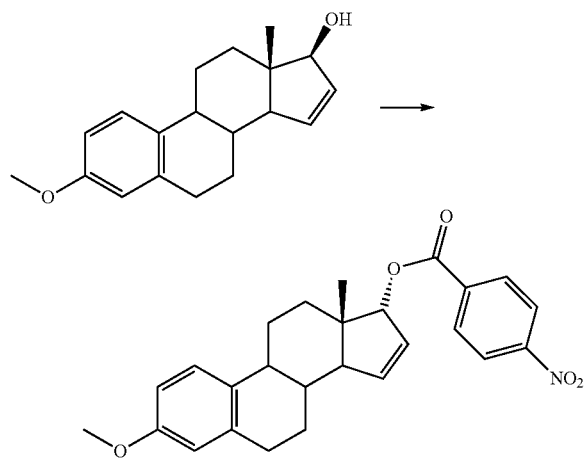

121 g triphenylphosphine, 27.1 g 4-nitrobenzoic acid, and 30.9 ml azodicarboxylic acid diisopropyl ester are added to a solution of 43.9 g of 3-methoxy-17β-hydroxyestra-1,3,5(10), 15-tetraene in 1.6 l tetrahydrofuran and it is stirred for 23° C. for 2 hours. Saturated sodium chloride solution is added, it is extracted with ethyl acetate, the combined organic extracts are washed with saturated sodium chloride solution and dried over sodium sulfate. The residue obtained after filtration and evaporation of the solvent is taken up in 1.2 l acetone, 80 ml of 30% hydrogen peroxide solution is added while cooling, and after 20 minutes it is poured, while cooling, into 600 ml of semiconcentrated sodium thiosulfate solution. It is extracted with ethyl acetate, the combined organic extracts are washed with saturated sodium chloride solution and dried over sodium sulfate. The residue obtained after filtration and evaporation of the solvent is purified by recrystallization. 52.5 g of the title compound is isolated.

EXAMPLE 2

Dienone Formation from Dienol Ether

17β-Hydroxy-15α,16α-methylene-19-nor-17α-pregna-4, 6-dien-3-one-21-carboxylic acid γ-lactone

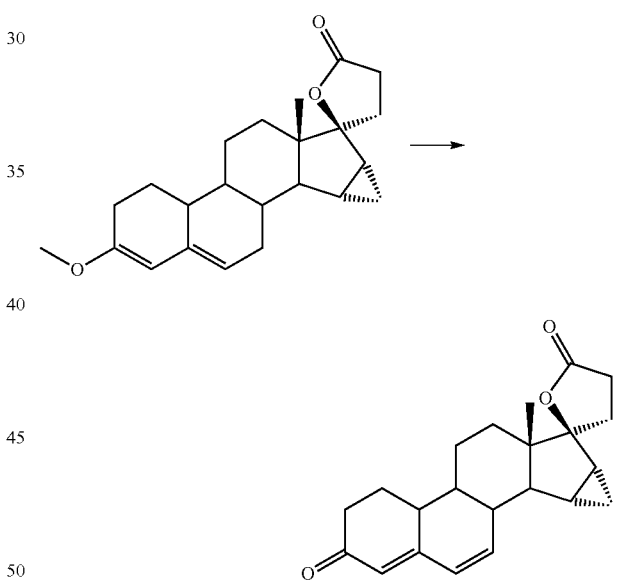

119 mg sodium acetate, 1.2 ml water and, in portions, a total of 460 g dibromohydantoin are added at −10° C. to a solution of 1.14 g of the compound prepared according to Example 2a in 2.1 ml N-methylpyrrolidone. After 30 minutes, 447 mg lithium bromide and 392 mg lithium carbonate are added and it is heated for 2.5 hours at a bath temperature of 100° C. It is poured into a mixture of ice and sodium chloride solution and the precipitated product is filtered off with suction. 910 mg of the title compound is isolated as a crystalline raw product, which can be reacted further directly.

$^1$H-NMR (CDCl$_3$): δ=0.59 (1H), 0.72 (1H), 1.00 (1H), 1.10 (1H), 1.19-1.59 (5H), 1.24 (3H), 1.79 (1H), 1.87 (1H), 1.99-2.59 (9H), 5.80 (1H), 6.24 (1H), 6.38 (1H) ppm.

EXAMPLE 2a

Dienol Ether Formation

17β-Hydroxy-3-methoxy-15α,16α-methylene-19-nor-17α-pregna-3,5-diene-21-carboxylicacid γ-lactone

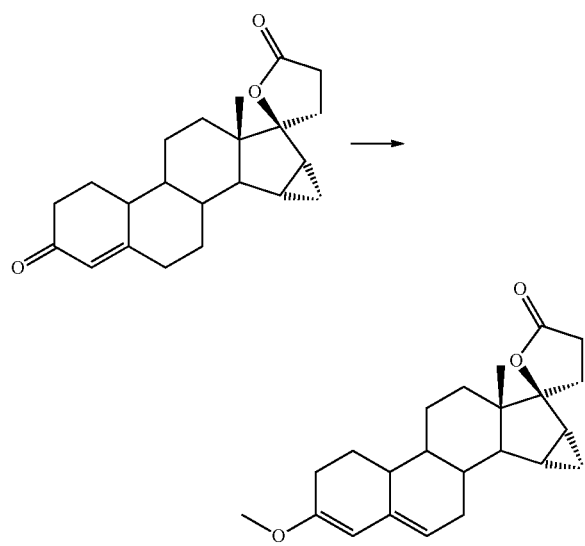

221 mg of pyridinium p-toluenesulfonate is added to a solution of 2 g of the compound prepared according to Example 1 in 29 ml 2,2-dimethoxypropane and it is heated under reflux for 4 hours. It is poured into saturated sodium hydrogencarbonate solution, extracted several times with ethyl acetate, the combined organic extracts are washed with saturated sodium chloride solution and dried over sodium sulfate. The residue obtained after filtration and evaporation of the solvent is purified by crystallization. 1.15 g of the title compound is isolated.

EXAMPLE 3

1,6-Addition (Methyl))

17β-Hydroxy-7α-methyl-15α,16α-methylene-19-nor-17α-pregna-4-en-3-one-21-carboxylicacid γ-lactone (A) and 17β-hydroxy-7β-methyl-15α,16α-methylene-19-nor-17α-pregna-4-en-3-one-21-carboxylic acid γ-lactone (B)

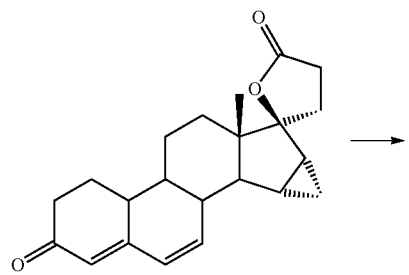

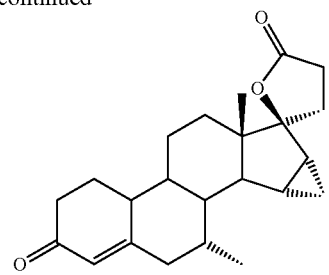

250 µl of a 3-molar solution of methylmagnesium chloride in tetrahydrofuran is added dropwise to a suspension of 7 mg copper(I) chloride in 1.2 ml tetrahydrofuran cooled to −30° C., and it is stirred for a further 10 minutes. It is cooled to −25° C. and the solution is added dropwise to 100 mg of the compound prepared according to Example 2 in 5 ml tetrahydrofuran. After 2 minutes it is poured into 1N hydrochloric acid, extracted several times with ethyl acetate, the combined organic extracts are washed with saturated sodium chloride solution and dried over sodium sulfate. The residue obtained after filtration and evaporation of the solvent is purified by chromatography. 23 mg of the title compound A is isolated along with a still contaminated mixture, which contains proportions of the title compound B.

$^1$H-NMR (CDCl$_3$) of A: δ=0.51 (1H), 0.66 (1H), 0.81 (3H), 0.94-1.10 (2H), 1.22 (3H), 1.18-1.60 (6H), 1.74-1.91 (3H), 2.00-2.58 (10H), 5.85 (1H) ppm.

EXAMPLE 4

17β-Hydroxy-7α-ethyl-15α,16α-methylene-19-nor-17α-pregna-4-en-3-one-21-carboxylic acid γ-lactone (A) and 17β-hydroxy-7β-ethyl-15α,16α-methylene-19-nor-17α-pregna-4-en-3-one-21-carboxylic acid γ-lactone (B)

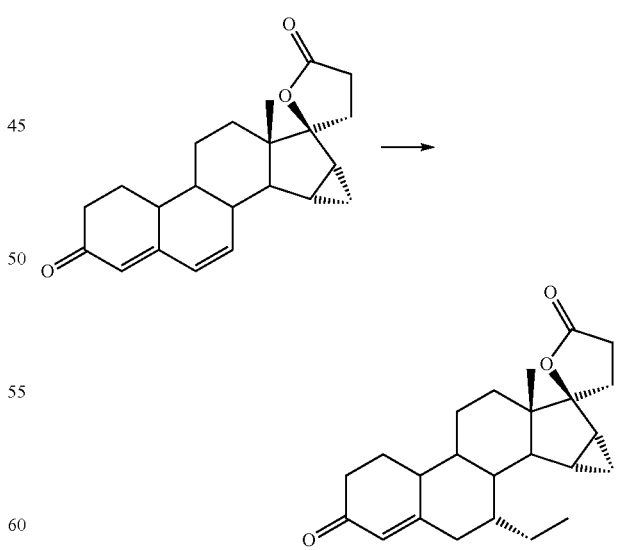

Similarly to Example 3, 200 mg of the compound prepared according to Example 2 using ethylmagnesium chloride is reacted and, after processing and purification, 81 mg of the title compound A is isolated along with a still contaminated mixture, which contains proportions of the title compound B.

¹H-NMR (CDCl₃) of A: δ=0.51 (1H), 0.75 (1H), 0.90 (3H), 0.95-1.10 (3H), 1.18-1.38 (4H), 1.22 (3H), 1.44 (1H), 1.50 (1H), 1.77-1.96 (4H), 2.01-2.10 (2H), 2.15 (1H), 2.22-2.54 (6H), 2.60 (1H), 5.86 (1H) ppm.

EXAMPLE 5

17β-Hydroxy-7α-vinyl-15α,16α-methylene-19-nor-17α-pregna-4-en-3-one-21-carboxylic acid γ-lactone (A) and 17β-hydroxy-7β-vinyl-15α,16α-methylene-19-nor-17α-pregna-4-en-3-one-21-carboxylic acid γ-lactone (B)

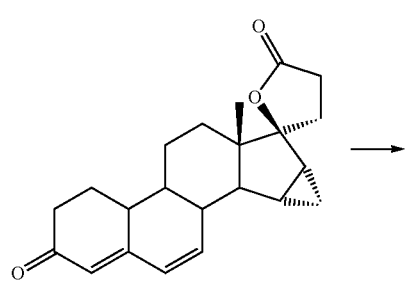

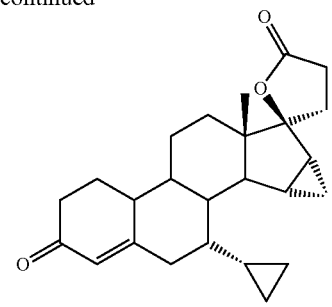

Similarly to Example 3, 210 mg of the compound prepared according to Example 2 using vinylmagnesium chloride is reacted and, after processing and purification, 16 mg of the title compound A is isolated along with a still contaminated mixture, which contains proportions of the title compound B.

¹H-NMR (CDCl₃) of A: δ=0.45 (1H), 0.63 (1H), 0.97-1.10 (2H), 1.16-1.36 (4H), 1.23 (3H), 1.40-1.57 (2H), 1.78-2.17 (5H), 2.22-2.54 (6H), 2.60 (1H), 2.79 (1H), 5.10 (1H), 5.18 (1H), 5.69 (1H), 5.88 (1H) ppm.

EXAMPLE 6

17β-Hydroxy-7α-cyclopropyl-15α,16α-methylene-19-nor-17α-pregna-4-en-3-one-21-carboxylic acid γ-lactone (A) and 17β-hydroxy-7β-cyclopropyl-15α,16α-methylene-19-nor-17α-pregna-4-en-3-one-21-carboxylic acid γ-lactone (B)

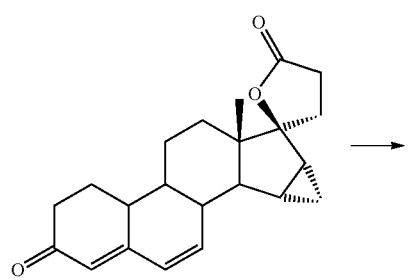

Similarly to Example 3, 200 mg of the compound prepared according to Example 2 using cyclopropylmagnesium bromide is reacted and, after processing and purification, 71 mg of the title compound A is isolated along with a still contaminated mixture, which contains proportions of the title compound B.

¹H-NMR (CDCl₃) of A: δ=-0.05 (1H), 0.41-0.53 (4H), 0.56 (1H), 0.99 (1H), 1.12 (1H), 1.16-1.32 (5H), 1.23 (3H), 1.43-1.57 (2H), 1.81-1.93 (3H), 2.02-2.21 (3H), 2.24-2.34 (2H), 2.38-2.57 (5H), 5.90 (1H) ppm.

EXAMPLE 7

6-hydroxymethyl

17β-Hydroxy-6β-hydroxymethyl-15α,16α-methylene-19-nor-17α-pregna-4-en-3-one-21-carboxylic acid γ-lactone

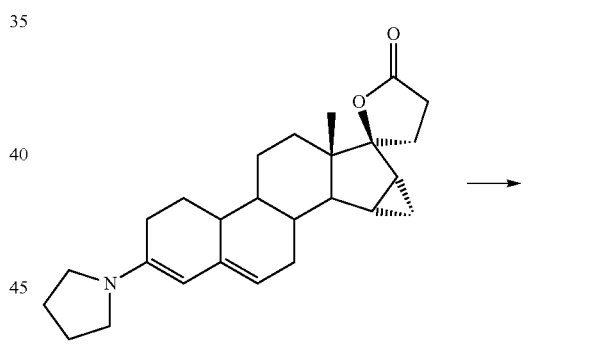

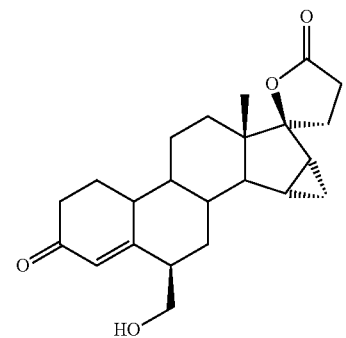

400 µl of 37% aqueous formaldehyde solution is added to a solution of 400 mg of the compound prepared according to Example 7a in a mixture of 4 ml toluene and 8 ml ethanol and it is stirred for 3 hours at 23° C. It is concentrated by evaporation and the residue is purified by chromatography. 180 mg of the title compound is isolated.

¹H-NMR (CDCl₃): δ=0.52 (2H), 0.75 (1H), 1.03 (1H), 1.21 (3H), 1.17-1.86 (10H), 1.97-2.56 (9H), 2.68 (1H), 3.73 (2H), 5.93 (1H) ppm.

EXAMPLE 7a

Dienamine for 6-alkylation

17β-Hydroxy-3-pyrrolidinyl-15α,16α-methylene-19-nor-17α-pregna-3,5-diene-21-carboxylicacid γ-lactone

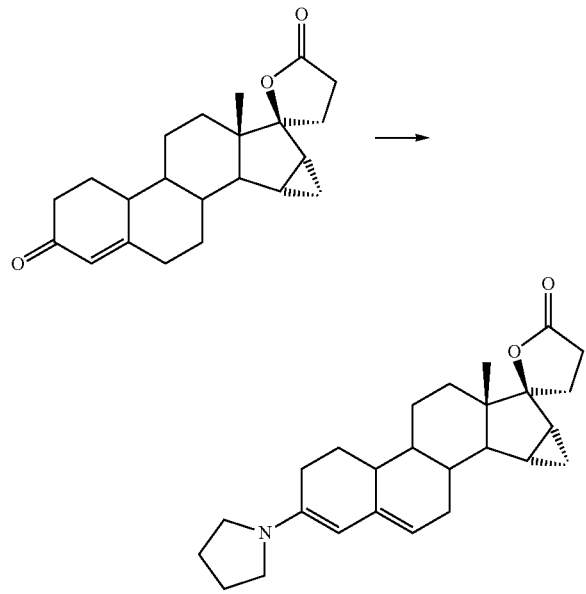

280 µl pyrrolidine is added to a solution of 500 mg of the compound prepared according to Example 1 in 5.3 ml methanol and it is heated under reflux for 2 hours. It is cooled, the precipitate is filtered off with suction, it is washed with a little cold methanol and 406 mg of the title compound is obtained, and this is reacted further without additional purification.

EXAMPLE 8

6-spirocyclopropanation (Corey)

6,6-(1,2-Ethanediyl)-17β-hydroxy-15α,16α-methylene-19-nor-17α-pregna-4-en-3-one-21-carboxylic acid γ-lactone

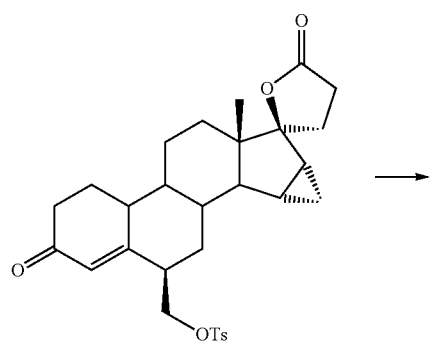

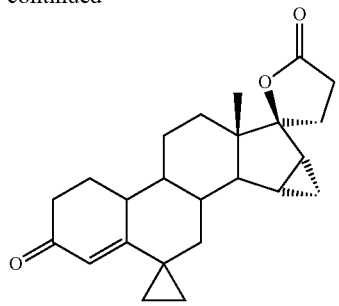

100 mg trimethylsulfoxonium iodide is dissolved in 1.0 ml dimethylsulfoxide, 18.5 mg of 60% sodium hydride dispersion is added and it is stirred for 2 hours at 23° C. Then a solution of 58 mg of the compound prepared according to Example 8a in 2.5 ml dimethylsulfoxide is added dropwise and it is stirred for a further 3.5 hours at 23° C. It is poured into water, extracted several times with ethyl acetate, the combined organic extracts are washed with water and saturated sodium chloride solution and dried over sodium sulfate. The residue obtained after filtration and evaporation of the solvent is purified by chromatography. 20 mg of the title compound is isolated.

¹H-NMR (CDCl₃): δ=0.43 (1H), 0.50 (1H), 0.53-0.62 (2H), 0.74 (1H), 0.85 (1H), 1.00 (1H), 1.17-1.37 (5H), 1.24 (3H), 1.42-1.53 (2H), 1.66 (1H), 1.78-1.88 (3H), 2.02 (1H), 2.09-2.32 (4H), 2.37-2.54 (3H), 5.70 (1H) ppm.

EXAMPLE 8a 6-tosyloxymethyl

17β-Hydroxy-6β-(p-tolylsulfonyloxymethyl)-15α,16α-methylene-19-nor-17α-pregna-4-en-3-one-21-carboxylic acid γ-lactone

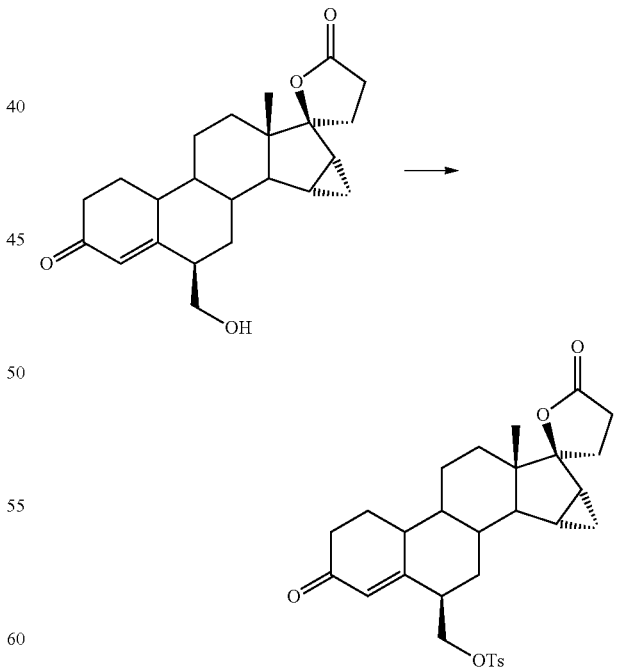

665 µl triethylamine and 190 mg p-toluenesulfonic acid chloride are added to a solution of 150 mg of the compound prepared according to Example 7 in 7.5 ml dichloromethane and it is stirred for 37 hours at 23° C. It is poured into saturated sodium carbonate solution, extracted several times with ethyl acetate, the combined organic extracts are washed with water and saturated sodium chloride solution and dried over sodium sulfate. The residue obtained after filtration and evaporation of the solvent is purified by chromatography. 131 mg of the title compound is isolated.

EXAMPLE 9

17β-Hydroxy-6β,7β-15α,16α-bismethylene-19-nor-17α-pregna-4-en-3-one-21-carboxylic acid γ-lactone (A) and 17β-hydroxy-6α,7α-15α,16α-bismethylene-19-nor-17α-pregna-4-en-3-one-21-carboxylic acid γ-lactone (B)

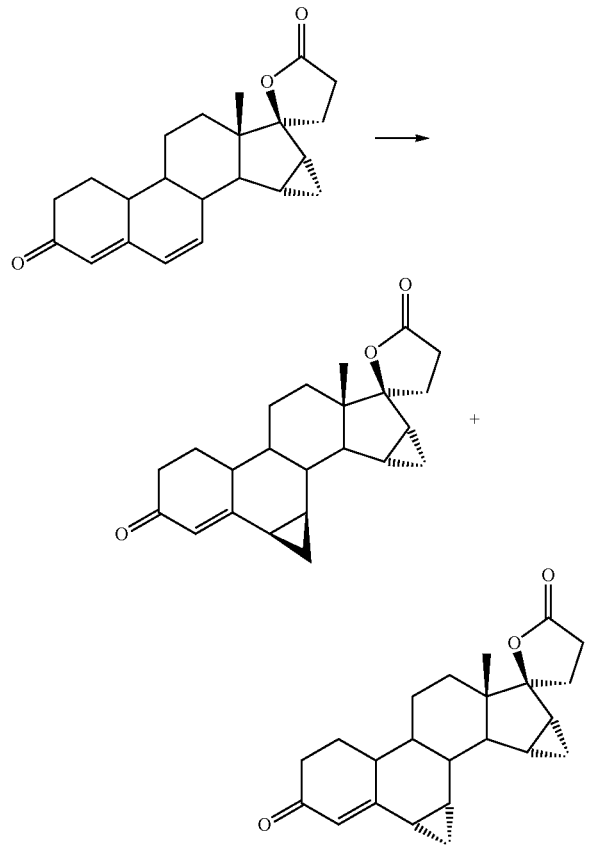

Similarly to Example 8, 1.13 g of the compound prepared according to Example 2 is reacted and, after processing and purification, 46 mg of the title compound A and 222 mg of the title compound B are isolated.

$^1$H-NMR (CDCl$_3$) of A: δ=0.58-0.68 (2H), 0.80-0.97 (2H), 1.09-1.37 (4H), 1.24 (3H), 1.43-1.96 (8H), 2.05-2.60 (8H), 6.15 (1H) ppm.

$^1$H-NMR (CDCl$_3$) of B: δ=0.60 (1H), 0.64-0.74 (2H), 0.95 (1H), 1.08 (1H), 1.14-1.51 (5H), 1.25 (3H), 1.66 (1H), 1.73-1.90 (3H), 1.98-2.58 (10H), 6.04 (1H) ppm.

EXAMPLE 10

Inert depot systems amenable to intrauterine implantation and composed of a biodegradable polymer or a synthetic silicone polymer consisting of an active ingredient-containing core in the appropriate polymer-active ingredient mixing ratio, surrounded by a polymer membrane ensuring the desired daily release rate, are introduced into the lumen of the rat uterus. The female animals are castrated beforehand and pretreated with estradiol for three days. The implants of different length (5-20 mm) and a restricted diameter (1.1 to 2 mm) remain for between 4 and 14 days in the rat uterus in order to investigate the local and systemic progestational effect of the released active ingredient on the basis of various parameters in different tissues. The following parameters are measured: 1) local progestational effect on the uterus on the basis of the weight of the uterus, the histologically detectable epithelial height and the expression of progestogen-regulated marker genes (e.g. IGFBP-1); 2) systemic progestational effect on the mammary gland on the basis of the expression of progestogen-regulated marker genes (e.g. RankL), 3) systemic progestational effect on the pituitary on the basis of the LH level (reduction in the estrogen-induced elevation of the LH level).

The compounds of the present invention show a significant progestational effect in the uterus which is comparable to a corresponding treatment with a levonorgestrel-containing depot system such as MIRENA®.

TABLE 1

| Ex. | Structure | Receptor binding | | | | | In vitro | | |
| --- | --- | --- | --- | --- | --- | --- | --- | --- | --- |
| | | Progesterone receptor | | Mineralo-corticoid receptor | Androgen receptor | | Transactivation Progesterone receptor | | |
| | | | | | | | Agonisten | Agonisten | |
| | | IC50 [nM] | Competition factor | Competition factor | IC50 [nM] | Competition factor | EC50 [nM] | Efficacy [%] | CF PR/ CF MR |
| A | (structure) | 43.3 | 2.7 | 0.5 | 630 | 37 | 88 | 72.2 | 5.40 |

TABLE 1-continued

| | | Receptor binding | | | | In vitro | | |
| | | Progesterone receptor | Mineralo-corticoid receptor | Androgen receptor | | Transactivation Progesterone receptor | | |
| | | | | | | Agonisten | Agonisten | |
| Ex. | Structure | IC50 [nM] | Competition factor | Competition factor | IC50 [nM] | Competition factor | EC50 [nM] | Efficacy [%] | CF PR/ CF MR |
|---|---|---|---|---|---|---|---|---|---|
| 1 | | 15 | 0.74 | 1.8 | 6 | 110.0 | 0.1 | 55.9 | 0.41 |
| 3 | | 12.1 | 0.60 | 1.3 | 61 | 2.8 | 0.6 | 87.0 | 0.46 |
| 4 | | 33 | 1.74 | 1.2 | 74 | 5.6 | 0.7 | 56.7 | 1.45 |
| 5 | | 15 | 1.16 | 1.4 | 55 | 3.0 | 3.4 | 66.1 | 0.83 |
| 6 | | 51 | 2.65 | 1.6 | 78 | 6.3 | 1.0 | 48.6 | 1.66 |

TABLE 1-continued

| Ex. | Structure | Receptor binding | | | | | In vitro | | |
|---|---|---|---|---|---|---|---|---|---|
| | | Progesterone receptor | | Mineralo-corticoid receptor | Androgen receptor | | Transactivation Progesterone receptor | | |
| | | | | | | | Agonisten | Agonisten | |
| | | IC50 [nM] | Competition factor | Competition factor | IC50 [nM] | Competition factor | EC50 [nM] | Efficacy [%] | CF PR/ CF MR |
| 7 | | 1100 | 49.90 | 2.1 | 10000 | 1000.0 | 910.0 | 22.8 | 23.76 |
| 8 | | 8.9 | 0.71 | 0.9 | 26 | 1.4 | 0.1 | 69.7 | 0.79 |
| 9 | | 16 | 0.86 | 0.7 | 420 | 38.5 | 1 | 77.4 | 1.16 |
| 9 | | 24 | 1.28 | 0.5 | 330 | 30.3 | 23 | 107.4 | 2.46 |

The compounds in Examples 1, 3-6 and 8-9 possess improved selectivity on the progesterone receptor (PR) compared with the mineralocorticoid receptor (MR) expressed by the ratio of the competition factors CF-PR/CF-MR. The ratios are in a range from 0.41 to 2.46 and are therefore well below that of DRSP (5.4).

The invention claimed is:

1. 15α,16α-Methylene-17-hydroxy-19-nor-17-pregna-4-en-3-one-21-carboxylic acid γ-lactone namely 17βHydroxy-15α,16α-methylene-19-nor-17α-pregna-4-en-3-one-21-carboxylic acid γ-lactone;
17β-Hydroxy-7α-methyl-15α,16α-methylene-19-nor-17α-pregna-4-en-3-one-21-carboxylic acid γ-lactone;
17β-Hydroxy-7β-methyl-15α,16α-methylene-19-nor-17α-pregna-4-en-3-one-21-carboxylic acid γ-lactone;
17β-Hydroxy-7α-ethyl-15α,16α-methylene-19-nor-17α-pregna-4-en-3-one-21-carboxylic acid γ-lactone;
17β-Hydroxy-7β-ethyl-15α,16α-methylene-19-nor-17α-pregna-4-en-3-one-21-carboxylic acid γ-lactone;
17β-Hydroxy-7α-vinyl-15α,16α-methylene-19-nor-17α-pregna-4-en-3-one-21-carboxylic acid γ-lactone;
17β-Hydroxy-7β-vinyl-15α,16α-methylene-19-nor-17α-pregna-4-en-3-one-21-carboxylic acid γ-lactone;
17β-Hydroxy-7α-cyclopropyl-15α,16α-methylene-19-nor-17α-pregna-4-en-3-one-21-carboxylic acid γ-lactone;
17β-Hydroxy-7β-cyclopropyl-15α,16α-methylene-19-nor-17α-pregna-4-en-3-one-21-carboxylic acid γ-lactone;
17β-Hydroxy-6-methylene-15α,16α-methylene-19-nor-17α-pregna-4-en-3-one-21-carboxylic acid γ-lactone;
17β-Hydroxy-6α-hydroxymethyl-15α,16α-methylene-19-nor-17α-pregna-4-en-3-one-21-carboxylic acid γ-lactone;
17β-Hydroxy-6α,7α,15α,16α-bismethylene-19-nor-17α-pregna-4-en-3-one-21-carboxylic acid γ-lactone;
17β-Hydroxy-6β,7β,15α,16α-bismethylene-19-nor-17α-pregna-4-en-3-one-21-carboxylic acid γ-lactone;
17β-Hydroxy-15α,16α-methylene-19-nor-17α-pregna-4,6-dien-3-one-21-carboxylic acid γ-lactone;
(E/Z)-3-(Hydroxyimino)-17β-hydroxy-15α,16α-methylene-19-nor-17α-pregna-4-ene-21-carboxylic acid γ-lactone;
(E/Z)-3-(Hydroxyimino)-17β-hydroxy-7α-methyl-15α,16α-methylene-19-nor-17α-pregna-4-ene-21-carboxylic acid γ-lactone;
(E/Z)-3-(Hydroxyimino)-17β-hydroxy-7β-methyl-15α,16α-methylene-19-nor-17α-pregna-4-ene-21-carboxylic acid γ-lactone;
(E/Z)-3-(Hydroxyimino)-17β-hydroxy-7α-ethyl-15α,16α-methylene-19-nor-17α-pregna-4-ene-21-carboxylic acid γ-lactone;
(E/Z)-3-(Hydroxyimino)-17β-hydroxy-7β-ethyl-15α,16α-methylene-19-nor-17α-pregna-4-ene-21-carboxylic acid γ-lactone;
(E/Z)-3-(Hydroxyimino)-17β-hydroxy-7α-vinyl-15α,16α-methylene-19-nor-17α-pregna-4-ene-21-carboxylic acid γ-lactone;
(E/Z)-3-(Hydroxyimino)-17β-hydroxy-7β-vinyl-15α,16α-methylene-19-nor-17α-pregna-4-ene-21-carboxylic acid γ-lactone;
(E/Z)-3-(Hydroxyimino)-17β-hydroxy-7α-cyclopropyl-15α,16α-methylene-19-nor-17α-pregna-4-ene-21-carboxylic acid γ-lactone;
(E/Z)-3-(Hydroxyimino)-17β-hydroxy-7β-cyclopropyl-15α,16α-methylene-19-nor-17α-pregna-4-ene-21-carboxylic acid γ-lactone;
(E/Z)-3-(Hydroxyimino)-17β-hydroxy-6-methylene-15α,16α-methylene-19-nor-17α-pregna-4-ene-21-carboxylic acid γ-lactone;
(E/Z)-3-(Hydroxyimino)-17β-hydroxy-6α-hydroxymethyl-15α,16α-methylene-19-nor-17α-pregna-4-ene-21-carboxylic acid γ-lactone;
(E/Z)-3-(Hydroxyimino)-17β-hydroxy-6β-hydroxymethyl-15α,16α-methylene-19-nor-17α-pregna-4-ene-21-carboxylic acid γ-lactone;
(E/Z)-3-(Hydroxyimino)-6,6-(1,2-ethanediyl)-17β-hydroxy-15α,16α-methylene-19-nor-17α-pregna-4-ene-21-carboxylic acid γ-lactone;
(E/Z)-3-(Hydroxyimino)-17β-hydroxy-6 α,7α,15α,16α-bismethylene-19-nor-17α-pregna-4-ene-21-carboxylic acid γ-lactone;
(E/Z)-3-(Hydroxyimino)-17β-hydroxy-6 β,7β,15α,16α-bismethylene-19-nor-17α-pregna-4-ene-21-carboxylic acid γ-lactone;
(E/Z)-3-(Hydroxyimino)-17β-hydroxy-15α,16α-methylene-19-nor-17α-pregna-4,6-diene-21-carboxylic acid γ-lactone;
17β-Hydroxy-18-methyl-15α,16α-methylene-19-nor-17α-pregna-4-en-3one-21-carboxylic acid γ-lactone;
17β-Hydroxy-7α-18-methyl-15α,16α-methylene-19-nor-17α-pregna-4-en-3one-21-carboxylic acid γ-lactone;
17β-Hydroxy-7β-18-methyl-15α,16α-methylene-19-nor-17α-pregna-4-en-3one-21-carboxylic acid γ-lactone;
17β-Hydroxy-7α-ethyl-18-methyl-15α,16α-methylene-19-nor-17α-pregna-4-en-3one-21-carboxylic acid γ-lactone;
17β-Hydroxy-7β-ethyl-18-methyl-15α,16α-methylene-19-nor-17α-pregna-4-en-3one-21-carboxylic acid γ-lactone;
17β-Hydroxy-7α-vinyl-18-methyl-15α,16α-methylene-19-nor-17α-pregna-4-en-3one-21-carboxylic acid γ-lactone;
17β-Hydroxy-7β-vinyl-18-methyl-15α,16α-methylene-19-nor-17α-pregna-4-en-3one-21-carboxylic acid γ-lactone;
17β-Hydroxy-7α-cyclopropyl-18-methyl-15α,16α-methylene-19-nor-17α-pregna-4-en-3one-21-carboxylic acid γ-lactone;
17β-Hydroxy-7β-cyclopropyl-18-methyl-15α,16α-methylene-19-nor-17α-pregna-4-en-3one-21-carboxylic acid γ-lactone;
17β-Hydroxy-6-methylene-18-methyl-15α,16α-methylene-19-nor-17α-pregna-4-en-3one-21-carboxylic acid γ-lactone;
17β-Hydroxy-6α-hydroxymethyl-18-methyl-15α,16α-methylene-19-nor-17α-pregna-4-en-3one-21-carboxylic acid γ-lactone;
17β-Hydroxy-6β-hydroxymethyl-18-methyl-15α,16α-methylene-19-nor-17α-pregna-4-en-3one-21-carboxylic acid γ-lactone;
17β-Hydroxy-6α,7α,15α,16α-bismethylene-19-nor-17α-pregna-4-en-3-one-21-carboxylic acid γ-lactone;
17β-Hydroxy-6β,7β,15α,16α-bismethylene-19-nor-17α-pregna-4-en-3-one-21-carboxylic acid γ-lactone;
17β-Hydroxy-18-methyl-15α,16α-methylene-19-nor-17α-pregna-4,6-dien-3-one-21-carboxylic acid γ-lactone;
(E/Z)-3-(Hydroxyimino)-17β-hydroxy-18-methyl-15α,16α-methylene-19-nor-17α-pregna-4-ene-21-carboxylic acid γ-lactone;
(E/Z)-3-(Hydroxyimino)-17β-hydroxy-7α-methyl-18-methyl-15α,16α-methylene-19-nor-17α-pregna-4-ene-21-carboxylic acid γ-lactone;

(E/Z)-3-(Hydroxyimino)-17β-hydroxy-7β-methyl-18-methyl-15α,16α-methylene-19-nor-17α-pregna-4-ene-21-carboxylic acid γ-lactone;

(E/Z)-3-(Hydroxyimino)-17β-hydroxy-7α-ethyl-18-methyl-15α,16α-methylene-19-nor-17α-pregna-4-ene-21-carboxylic acid γ-lactone;

(E/Z)-3-(Hydroxyimino)-17β-hydroxy-7β-ethyl-18-methyl-15α,16α-methylene-19-nor-17α-pregna-4-ene-21-carboxylic acid γ-lactone;

(E/Z)-3-(Hydroxyimino)-17β-hydroxy-7α-vinyl-18-methyl-15α,16α-methylene-19-nor-17α-pregna-4-ene-21-carboxylic acid γ-lactone;

(E/Z)-3-(Hydroxyimino)-17β-hydroxy-7β-vinyl-18-methyl-15α,16α-methylene-19-nor-17α-pregna-4-ene-21-carboxylic acid γ-lactone;

(E/Z)-3-(Hydroxyimino)-17β-hydroxy-7α-cyclopropyl-18-methyl-15α,16α-methylene-19-nor-17α-pregna-4-ene-21-carboxylic acid γ-lactone;

(E/Z)-3-(Hydroxyimino)-17β-hydroxy-7β-cyclopropyl-18-methyl-15α,16α-methylene-19-nor-17α-pregna-4-ene-21-carboxylic acid γ-lactone;

(E/Z)-3-(Hydroxyimino)-17β-hydroxy-6-methylene-18-methyl-15α,16α-methylene-19-nor-17α-pregna-4-ene-21-carboxylic acid γ-lactone;

(E/Z)-3-(Hydroxyimino)-17β-hydroxy-6α-hydroxymethyl-18-methyl-15α,16α-methylene-19-nor-17α-pregna-4-ene-21-carboxylic acid γ-lactone;

(E/Z)-3-(Hydroxyimino)-17β-hydroxy-6β-hydroxymethyl-18-methyl-15α,16α-methylene-19-nor-17α-pregna-4-ene-21-carboxylic acid γ-lactone;

(E/Z)-3-(Hydroxyimino)-6,6-(1,2-ethanediyl)-17β-hydroxy-18-methyl-15α,16α-methylene-19-nor-17α-pregna-4-ene-21-carboxylic acid γ-lactone;

(E/Z)-3-(Hydroxyimino)-17β-hydroxy-6α,7α,15α,16α-bismethylene-19-nor-17α-pregna-4-ene-21-carboxylic acid γ-lactone;

(E/Z)-3-(Hydroxyimino)-17β-hydroxy-6β,7β,15α,16α-bismethylene-19-nor-17α-pregna-4-ene-21-carboxylic acid γ-lactone; or (E/Z)-3-(Hydroxyimino)-17β-hydroxy-18-methyl-15α,16α-methylene-19-nor-17α-pregna-4,6-diene-21-carboxylic acid γ-lactone.

2. A medicinal product containing at least one 15α,16α-methylene-17-hydroxy-19-nor-17-pregna-4-en-3-one-21-carboxylic acid γ-lactone derivative according to claim 1 and at least one pharmaceutically acceptable excipient.

3. The medicinal product as claimed in claim 2, further comprising at least one estrogen.

4. The medicinal product as claimed in claim 3, characterized in that the estrogen is ethinylestradiol.

5. The medicinal product as claimed in claim 3, characterized in that the estrogen is a natural estrogen.

6. The medicinal product as claimed in claim 5, characterized in that the natural estrogen is estradiol.

7. The medicinal product as claimed in claim 5, characterized in that the natural estrogen is estradiolvalerate.

8. The medicinal product as claimed in claim 5, characterized in that the natural estrogen is a conjugated estrogen.

9. A method of oral contraception comprising the step of administering a 15α,16α-methylene-17-hydroxy-19-nor-17-pregna-4-en-3-one-21-carboxylic acid γ-lactone derivative of claim 1 to a women in need thereof.

* * * * *